US012758761B2

(12) United States Patent
Forsell

(10) Patent No.: US 12,758,761 B2
(45) Date of Patent: Oct. 13, 2026

(54) BLOOD CLOT REMOVAL DEVICE, SYSTEM, AND METHOD

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 252 days.

(21) Appl. No.: 18/499,253

(22) Filed: Nov. 1, 2023

(65) Prior Publication Data

US 2024/0058736 A1 Feb. 22, 2024

Related U.S. Application Data

(63) Continuation of application No. 16/984,368, filed on Aug. 4, 2020, now Pat. No. 11,839,848, which is a (Continued)

(51) Int. Cl.
*A61M 60/50* (2021.01)
*A61F 2/00* (2006.01)

(Continued)

(52) U.S. Cl.
CPC ........... *A61M 60/50* (2021.01); *A61F 2/0036* (2013.01); *A61M 1/71* (2021.05); *A61M 1/79* (2021.05); *A61M 1/82* (2021.05); *A61M 27/002* (2013.01); *A61M 60/857* (2021.01); *A61F 2/482* (2021.08); *A61F 2/484* (2021.08); *A61F 2250/0001* (2013.01); *A61F 2250/0002* (2013.01); *A61M 1/72* (2021.05); *A61M 2027/004* (2013.01);

(Continued)

(58) Field of Classification Search
CPC ...... B01D 46/68; B01D 46/681; B01D 46/66; B01D 46/79; B01D 46/86; B01D 46/88; B01D 46/90; A61F 2/0036; A61F 2/482; A61F 2/484; A61F 2250/0001; A61F 2250/0002; A61M 1/71; A61M 1/79; A61M 1/82; A61M 27/002; A61M 60/50; A61M 60/857; A61M 60/871; A61M 1/72; A61M 27/006; A61M 60/00; A61M 60/122; A61M 2027/004; A61M 2205/10; A61M 2205/3331; A61M 2205/3523; A61M 2210/1021; A61M 2210/1078; A61M 2205/7554; A61M 1/34; A61M 1/3633; A61M 1/3666; A61M 1/3403
See application file for complete search history.

(56) References Cited

U.S. PATENT DOCUMENTS 4,994,188 A * 2/1991 Prince ..................... A61M 1/36 210/636
5,902,336 A * 5/1999 Mishkin .................. A61M 1/34 604/27

(Continued)

*Primary Examiner* — Ashley L Fishback
*Assistant Examiner* — Chima U Igboko
(74) *Attorney, Agent, or Firm* — The Roy Gross Law Firm, LLC; Roy Gross

(57) ABSTRACT

The present invention relates to an implantable cassette for holding filters. The cassette is provided with a revolving compartment having a plurality of segments. Each segment is for holding a filter for filtering blood. Also provided is attachment means for attaching the cassette to a blood flow passageway to thereby allow blood to flow through a first segment of the revolving compartment. An operation device for revolving the revolving compartment, to thereby move the first segment out of the blood flow passageway, is also provided.

20 Claims, 15 Drawing Sheets

Related U.S. Application Data continuation of application No. 12/864,828, filed as application No. PCT/SE2009/000040 on Jan. 28, 2009, now Pat. No. 10,729,984.

(60) Provisional application No. 61/006,711, filed on Jan. 28, 2008.

(51) Int. Cl.

| | |
|---|---|
| ***A61M 1/00*** | (2006.01) |
| ***A61M 27/00*** | (2006.01) |
| ***A61M 60/857*** | (2021.01) |
| *A61F 2/48* | (2006.01) |
| *A61M 60/00* | (2021.01) |
| *A61M 60/122* | (2021.01) |
| *A61M 60/871* | (2021.01) |

(52) U.S. Cl.

CPC ........... *A61M 27/006* (2013.01); *A61M 60/00* (2021.01); *A61M 60/122* (2021.01); *A61M 60/871* (2021.01); *A61M 2205/10* (2013.01); *A61M 2205/3331* (2013.01); *A61M 2205/3523* (2013.01)

(56) References Cited

U.S. PATENT DOCUMENTS

| | | | | | |
|---|---|---|---|---|---|
| 5,957,672 | A * | 9/1999 | Aber | A61M 60/237 | 417/423.12 |
| 7,488,302 | B1 * | 2/2009 | Helm | A61M 1/34 | 604/6.11 |
| 2004/0254514 | A1 * | 12/2004 | Gura | A61M 1/34 | 977/905 |

* cited by examiner

Fig. 31a
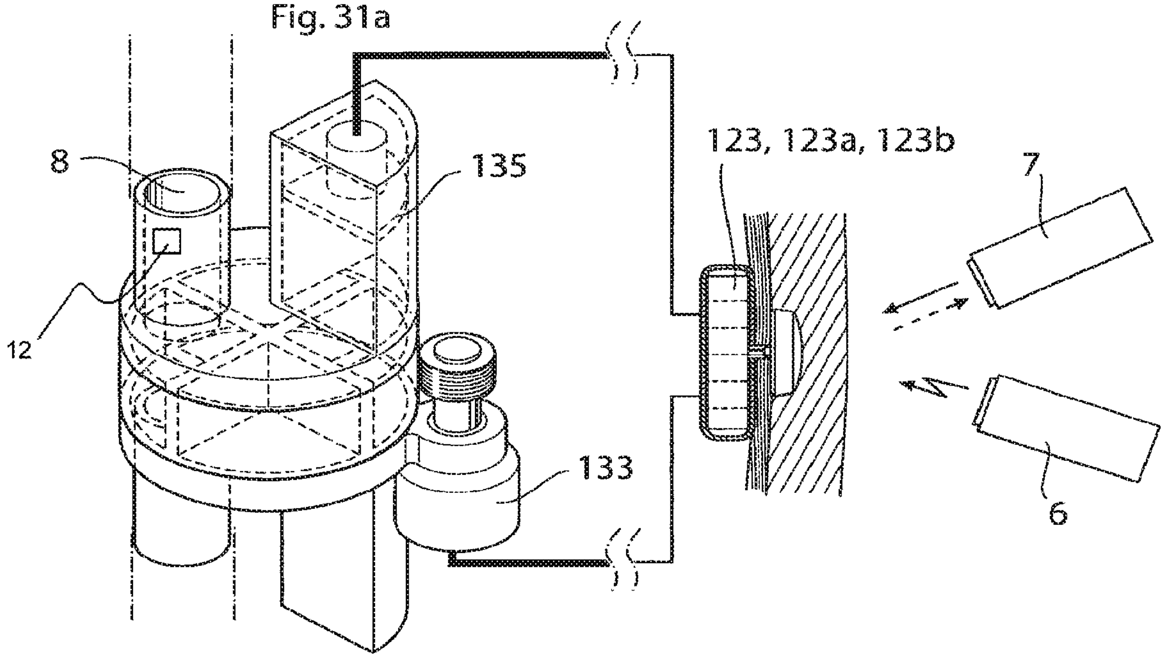
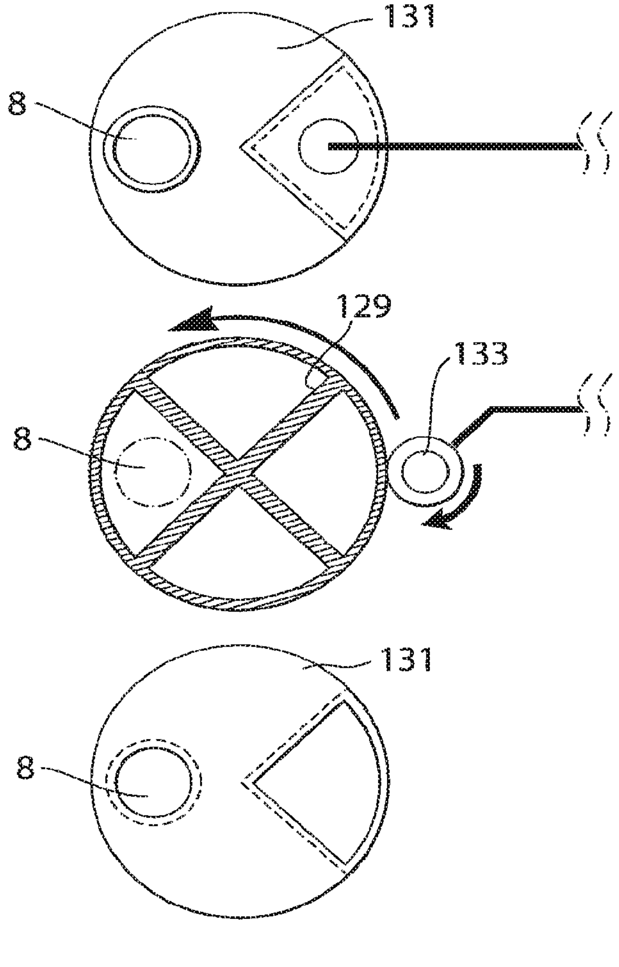
Fig. 31b

BLOOD CLOT REMOVAL DEVICE, SYSTEM, AND METHOD

This application is a continuation of U.S. patent application Ser. No. 16/984,368, filed Aug. 4, 2020, which is a continuation of U.S. patent application Ser. No. 12/864,828, filed on Jul. 27, 2010, and issued as U.S. Pat. No. 10,729,894, which is the U.S. national phase of International Application No. PCT/SE2009/000040, filed Jan. 28, 2009, which designates the U.S. and claim priority to U.S. Application No. 61/006,711, filed Jan. 28, 2008, the entire contents of each of which are hereby

FIELD OF INVENTION

The present invention relates generally to a device and a system implantable in a blood flow passageway of a human or mammal patient for removing blood clots, and more particularly to a system for removing blood clots in a vascular system, of the patient, one example being a heart pump system. The invention also relates to a method of removing blood clots.

BACKGROUND

Today many implants are provided where the blood comes into contact with foreign material. All such implants have an associated risk of triggering blood clots. Such clots may become loose and may create severe damages at other parts of the body. Blood clots reaching the brain are the most dangerous ones and implants in the heart region may therefore be a first priority (although not limited to) of a blood clot removal system. One example of such implants and one example of use for the blood clot removal system may be heart help pumps. When a person has heart failure, his or her heart can't pump enough blood to meet the body's needs. In some cases, an advanced treatment such as a heart pump may be recommended. A heart pump takes over the function of one or both of the heart's lower chambers, with the potential to improve your symptoms and quality of life. Once considered a last resort for prolonging life until a donated heart became available, heart pumps have become a possible long-term treatment for selected people with heart failure.

A heart pump either takes over or assists the pumping role of the left ventricle—the heart's main pumping chamber. Part of the device, such as an electronic pump, is implanted in the heart and abdomen, and part, such as an electronic control unit, remains outside your body. An energy supply, such as a battery, can be provided either outside the body or be implanted.

One tube carries blood from the left ventricle of the heart and into the pump. Another tube takes blood pumped from the device into the artery to be circulated throughout the body.

A heart pump can be a lifesaving treatment. However, the potential risks are serious, including the risk of having blood clots in the arteries leading from the heart.

Many other implants may be used together with the blood clot removal system. Basically any implant in contact with blood may be targets for the invention.

SUMMARY OF THE INVENTION

An object of the present invention is to provide a device, a system, and a method for removing blood clots in the vascular system of a patient.

The invention is based on the realization that a blood clot removal device can be implanted in a patient instead of being external of the patient.

According to a first aspect of the present invention there is provided a blood clot removal device for removing blood clots from the vascular system of a patient, the blood clot removal device being implantable in the patient's body and comprising a blood flow passageway, a filter provided in the blood flow passageway for filtering blood clots, and a cleaning device for cleaning the filter. One possibility is to clean the filter mechanically.

The cleaning device preferably is adapted to move blood clots away from the blood flow passageway to a place free inside the patient's body, where the body itself will take care of the blood clots. Alternatively, a collecting volume, such as a bag, is provided for collecting cleaned blood that has been mechanically cleaned from the filter. Most likely such a bag will then be placed inside the body.

In a preferred embodiment, the cleaning device is adapted to slice, push or scratch away any clots from the filter, but the cleaning device can also suck away any clots from the filter.

In one embodiment, the cleaning device comprises a first piston, with preferably is provided with a first recess in an outer end portion thereof to collect blood clots removed from the filter. By providing the first piston with a plurality of channels for accommodating the filter in an extended position of the first piston, it can surround the filter, ensuring essentially complete removal of blood clots therefrom. This is preferably effected if the first piston is movable in a direction perpendicular to the direction of the blood flow passageway.

The movement of the first piston can be controlled by a source of pressurized air, ensuring rapid acceleration of the first piston and thereby short cleaning cycles. The movement of the first piston can alternatively be controlled by an electric motor, a solenoid or the like.

The filter is of biocompatible material in order to avoid unnecessary interference with the blood environment.

In one embodiment, the blood clot removal device is used in a system comprising a heart pump connected to the blood flow passageway, wherein a first tube preferably connects the heart pump to the left ventricle of the patient's heart and a second tube connects the heart pump connected to the patient's aorta.

The filter preferably comprises a plurality of strips, which may be equally spaced to form a filter for blood clots. In order to achieve a filtering function, the distance between two adjacent strips is preferably less than 2 millimeters, and even more preferably less than 1.0 millimeter. The distance depends on which size blood clots you want to avoid.

In one embodiment, a second piston is provided across the blood flow passageway from the first piston, wherein the second piston is movable in a direction essentially perpendicular to the direction of the blood flow passageway and spring biased in the direction of the first piston. If an outer end portion of the second piston is provided with a second recess, the first piston and the second piston cooperate to catch blood clots for further removal. This further removal can be accomplished by means of a third piston, which is movable in a direction perpendicular to both the direction of the blood flow passageway and the direction of movement of the first piston and of the second piston.

In a preferred embodiment, the blood flow passageway of the blood clot removal device has an essentially square cross-sectional shape, which provides for a laminated flow of the blood, particularly if the square shape is combined with a filter comprising parallel strips.

The blood clot removal device is in a preferred embodiment insertable in a blood vessel of the patient, preferably via surgery.

The blood clot removal device can be adapted to be placed in the patient's abdomen or thorax.

The blood clot removal device is preferably comprised in a system for removing blood clots of a patient. This system can comprise a switch, preferably a subcutaneous switch being adapted to manually and non-invasively control any function of the blood clot removal device.

The system for removing blood clots preferably comprises a hydraulic device having a hydraulic reservoir, wherein the blood clot removal device is adapted to non-invasively be regulated by manually pressing the hydraulic reservoir.

A wireless remote control can non-invasively regulate any function of the blood clot removal device. Even more important any function of the device may be programmable by such a remote control.

Also, a wireless energy transmitter can non-invasively energize the blood clot removal device.

An energy source is preferably adapted to power the blood clot removal device. The energy source can comprise an internal energy source, such as an internal energy source adapted to receive energy from an external energy source transmitting energy in a wireless mode. The internal energy source can then be charged from the energy in the wireless mode.

The system preferably comprises a feedback device for sending information from inside the patient's body to the outside thereof to give feedback information related to at least one functional parameter of the device or a physical parameter of the patient, thereby optimizing the performance of the system. One preferred functional parameter of the device is correlated to the transfer of energy for charging the internal energy source.

The system preferably comprises an operation device for operating the blood clot removal device. This operation device can comprise a motor or a pump, an electrically powered operation device, a hydraulic operation device, or an electric motor.

To improve the performance of the system for removing blood clots, a physical parameter sensor, such as a pressure sensor, is provided for sensing a physical parameter of the patient. An internal control unit can act in response to the physical parameter sensed by the sensor.

A functional parameter sensor sensing a functional parameter of the blood clot removal device can also be provided. An internal control unit acting in response to the functional parameter sensed by the sensor can also be provided.

A method of using the system for removing blood clots is also provided, wherein at least one function of the blood clot removal device is regulated from outside the patient's body. The regulation is in a preferred embodiment non-invasively by manually pressing a subcutaneous switch. In an alternative embodiment, non-invasively regulation are performed by manually pressing a hydraulic reservoir connected to the blood clot removal device.

Alternatively, the system for removing blood clots comprises a wireless remote control, wherein non-invasively regulation is performed using said remote control.

In a preferred embodiment, the system for removing blood clots comprises a wireless energy transmitter, wherein non-invasively regulation is performed using said energy transmitter.

Preferably, an energy source is used for powering and adjusting any function of the blood clot removal device. The energy source may comprise an internal energy source, which preferably is associated with an external energy source adapted to transmit wireless energy. Energy is preferably transmitted from the external energy source to charge the internal energy source. Feedback information is preferably sent from inside the body to the outside thereof to give feed back related to the functional parameters of the device or physical parameters of the patient. The functional parameter of the device is correlated to the transfer of energy for charging the internal energy source.

In one embodiment, wireless energy is transmitted for powering the operation device.

In a preferred embodiment, the method of using a system for removing blood clots comprises the steps of: implanting an implantable source of energy in the patient, providing an external source of energy, controlling the external source of energy to release wireless energy, charging non-invasively the implantable source of energy with the wireless energy, controlling the implantable source of energy from outside the patient's body, and releasing energy for use in connection with operation of the blood clot removal device. The wireless energy is preferably stored in the implantable source of energy.

In another preferred embodiment, the method of using a system for removing blood clots comprises the steps of: providing an external source of energy outside the patient's body, and controlling the external source of energy from outside the patient's body to release wireless energy, and using released wireless energy for operating the operation device. The wireless energy is preferably transformed into electrical energy inside the patient's body using an implanted energy-transforming device and using the electrical energy when operating the blood clot removal device.

In one embodiment, the electrical energy is used directly in connection with operation of the blood clot removal device, as a transforming device transforms the wireless energy into the electrical energy.

In another embodiment, the external source of energy is controlling from outside the patient's body to release non-magnetic wireless energy, and released non-magnetic wireless energy is used for operating the blood clot removal device.

In yet an alternative embodiment, the external source of energy is controlled from outside the patient's body to release electromagnetic wireless energy, and released electromagnetic wireless energy is used for operating the blood clot removal device.

A method for placing a blood clot removal device, comprising a surgical method via a laparoscopic abdominal approach, comprises the steps of: inserting a needle or tube like instrument into the abdomen of the patient's body, using the needle or tube like instrument to fill the patient's abdomen with gas thereby expanding the patient's abdominal cavity, placing at least two laparoscopic trocars in the patient's body, inserting a camera through one of the trocars into the patient's abdomen, inserting at least one dissecting tool through a trocar and dissecting the intended placement area of the patient, placing at least one blood clot removal device in any part of the vascular system in the abdomen, moving blood clots away from the vascular system post operatively to a different part of the body, and powering the device with a source of energy. The blood clots can be moved either to a place that is free in the abdomen, to a place that is free in the abdomen, or to a place that is encapsulated in a closed bag in the abdomen The blood clot removal device is preferably programmable from outside the patients body. By adding the steps of sensing a physical parameter of the patient or a functional parameter of the device, and sending sensing information to an internal control unit adapted for regulating said blood clot removal device, performance is improved.

A method of placing a blood clot removal device, comprising a surgical method via a laparoscopic thoraxial approach, comprises the steps of: inserting a needle or tube like instrument into the thorax of the patients body, using the needle or tube like instrument to fill the thorax with gas thereby expanding the thoraxical cavity, placing at least two laparoscopic trocars in the patient's body, inserting a camera through one of the trocars into the thorax, inserting at least one dissecting tool through a trocar and dissecting the intended area of the patient, placing at least one blood clot removal device in any part of the vascular system in the thorax, moving blood clots away from vascular system post operatively to a different part of the body, and powering the device with a source of energy. The blood clots can be moved either to a place that is free in the thorax, to a place that is free in the abdomen, or to a place that is encapsulated in a closed bag in the thorax The device is preferably programmed from outside the body of the patient.

A method for surgically treating a patient needing a blood clot removal device in the vascular system in the patient's abdomen comprises the steps of: cutting an opening in the patient's abdominal wall, dissecting an area of the vascular system, placing a blood clot removal device inside the vascular system, and suturing said abdominal wall. In one embodiment, blood clots are moved away from the vascular system into an encapsulated closed bag in the patient's abdomen by means of the blood clot removal device. In another embodiment, blood clots are moved to the free abdomen.

A method for surgically treating a patient needing a blood clot removal device in the vascular system in the thorax comprises the steps of: cutting an opening in the thorax wall, dissecting the area of the vascular system, placing a blood clot removal device inside the vascular system, and suturing said thorax wall. A step of moving blood clots away from the vascular system can comprise moving blood clots either to a place that is free in the thorax, to a place that is free in the abdomen, or to a place that is encapsulated in a closed bag in the thorax A method using an system for removing blood clots, for postoperatively and non-invasively regulating the blood clot removal device, comprises the steps of: moving any blood clots, which have been accumulated in the vascular system of the patient's body, away from the vascular system, and placing the blood clots outside the vascular system. This can be accomplished by an energy source, preferably repeatedly according to a pre-programmed time-schedule. The steps of moving any blood clots away from the vascular system and placing the blood clots outside the vascular system are preferably repeated and at least partly controlled by an internal control unit getting input from a sensor sensing any physical parameter of the patient or any functional parameter of the device. The accumulation of blood clots in the filter may be visualized with light sensors, sensors measuring any electrical parameter, any blood flow measurement, pressure difference before and after the filter or any other kind of sensor.

An operation method for surgically placing a blood clot removal device comprises the steps of: cutting the patient's skin, dissecting a placement area where to place the blood clot removal device inside the vascular system in the abdomen or thorax or retroperitoneal or subcutaneously or any limb of the patient, placing the blood clot removal device in the placement area, removing, postoperatively and non-invasively without penetrating the patent's skin, any blood clots from the vascular system to outside thereof, and using energy from an energy source without any penetration through the patient's skin to power the blood clot removal device.

Further preferred embodiments are defined by the dependent claims.

BRIEF DESCRIPTION OF DRAWINGS

The invention is now described, by way of example, with reference to the accompanying drawings, in which:

FIGS. 31*a* and 31*b* are views of a filter cassette.

DETAILED DESCRIPTION OF PREFERRED EMBODIMENTS

Figure 1:
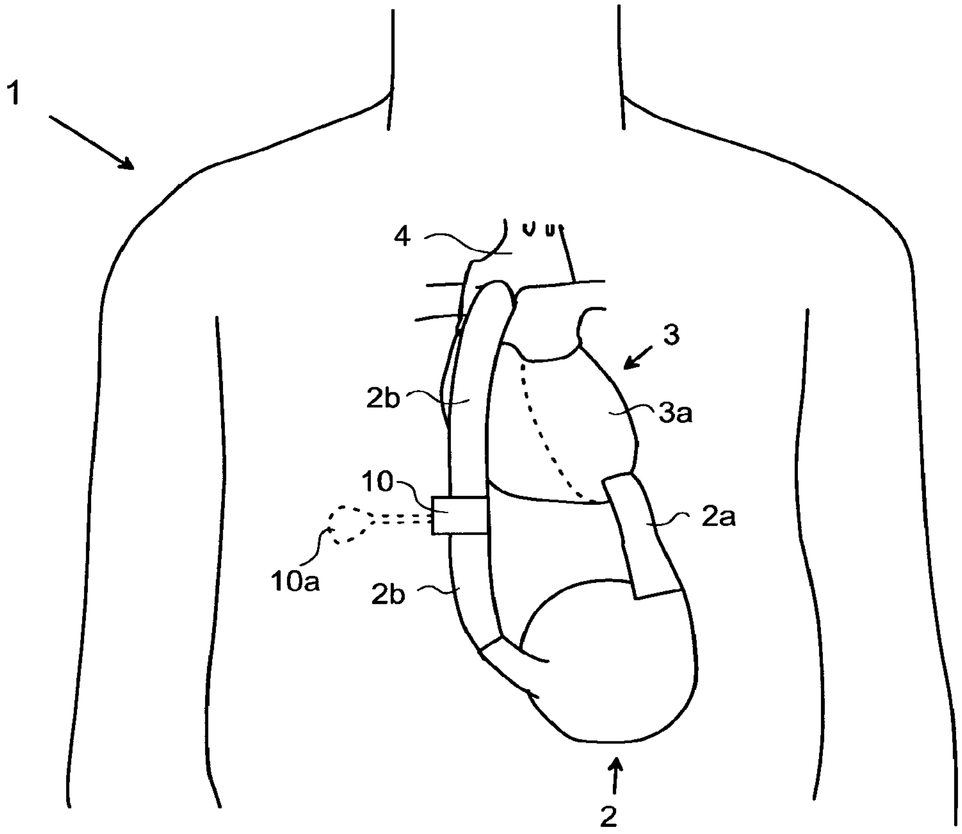
FIG. 1 is an overview of the body of a patient having an implanted heart pump.

In the following a detailed description of preferred embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

FIG. 1 shows a patient 1 having an implanted heart pump 2. The implanted heart pump 2 is connected to the left ventricle 3*a* of the patient's heart 3 by means of a first tube 2*a*. The heart pump 2 is also connected to the aorta, generally designated 4, of the patient 1 by means of a second tube 2*b*. In this way, during operation the heart pump supplements or replaces the blood pumping operation of the patient's heart 3.

A blood clot removal device 10 according to the invention is shown provided in the second tube 2*b* of the heart pump 2, i.e., in the tube leading to the aorta 4 of the patient 1. This means that part of the blood flow passageway provided by the second tube 2*b* is replaced by a blood flow passageway in the blood clot removal device 10. The blood clot removal device 10 is thus an artificial device insertable in an artificial blood vessel of the patient. The function of the clot removal device is to remove any blood clots in the blood transported by the second tube 2*b*. These blood clots are preferably moved to a place free inside the body of the patient. However, they could alternatively be collected in a collecting volume, such as a bag 10*a* connected to the blood clot removal device 10 for subsequent removal or storage. A preferred storage capacity of the bag 10*a* can be more than 100 milliliters, for example. The blood clot removal device is an artificial device but could be inserted directly into a blood vessel of the patient or connected between two ends of a blood vessel.

The clot removal device is preferably insertable in a blood flow passageway of the patient via surgery and is placed in the patient's abdomen or thorax or cephalic or neck region or retroperitoneal or any limb of the patient.

Figure 2:
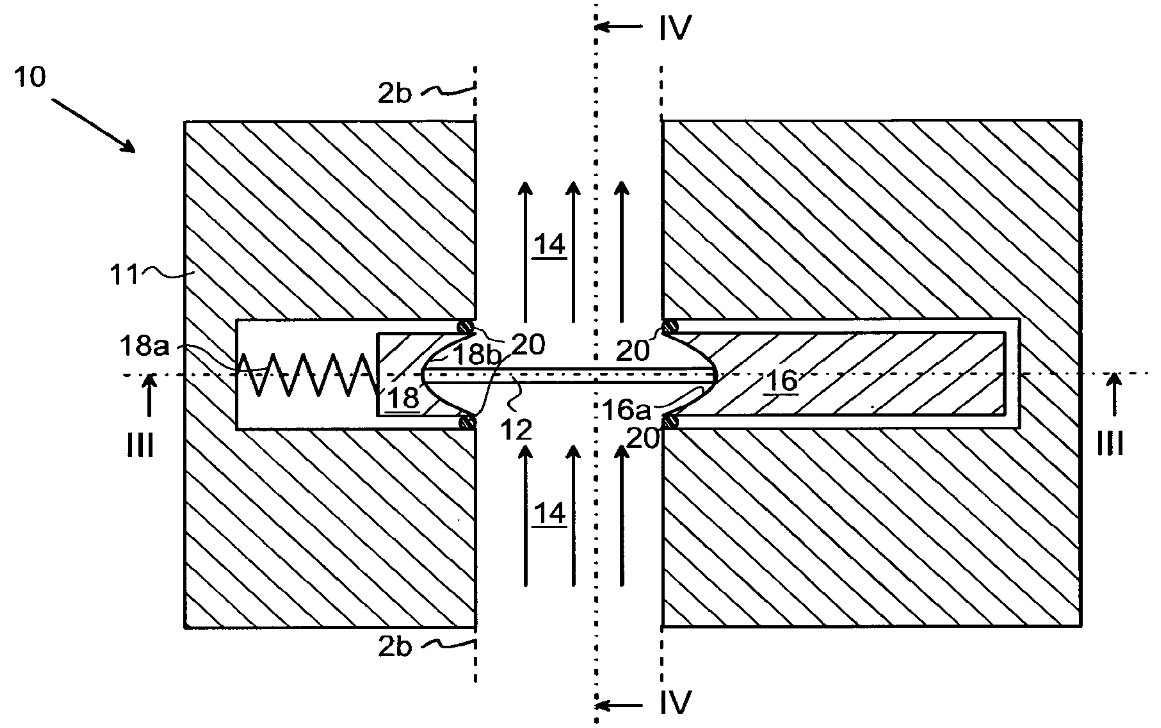
FIG. 2 is a sectional view of a clot removal device according to the invention.
Figure 3:
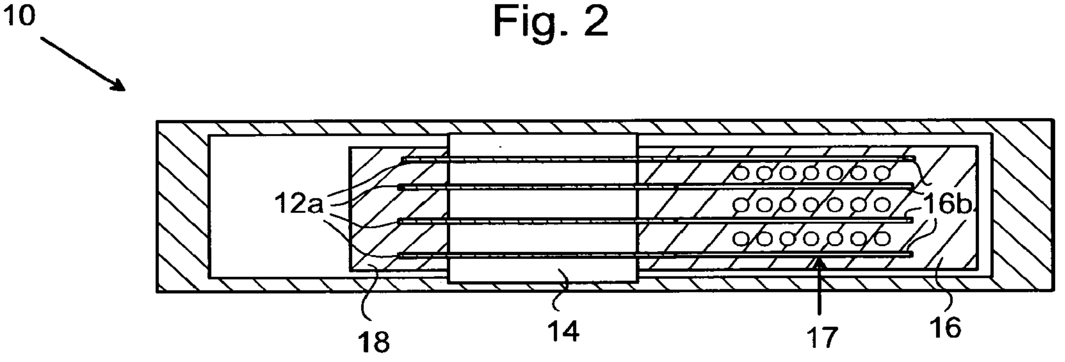
FIG. 3 is a cross sectional view of the clot removal device of FIG. 2 taken along the line III-III before a cleaning operation.
Figure 4:
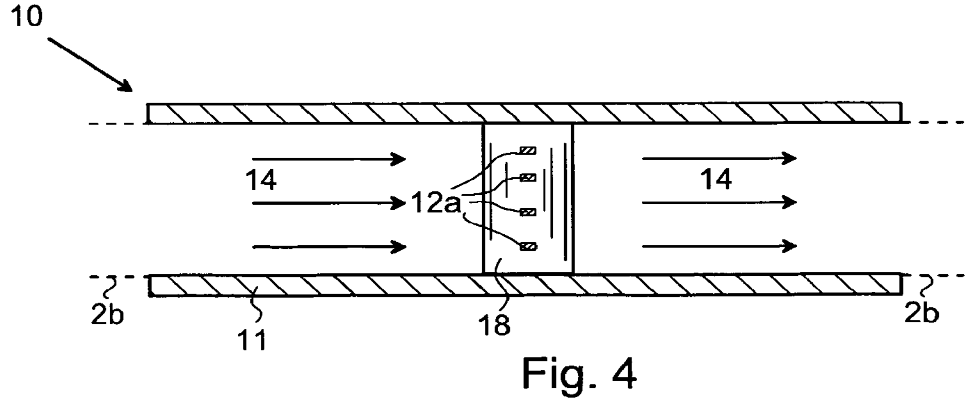
FIG. 4 is a sectional view of the clot removal device of FIG. 2 taken along the line IV-IV.

The design of a first preferred embodiment of the blood clot removal device 10 will now be described in detail, with reference to FIGS. 2-4. FIG. 2 shows a sectional view wherein the blood clot removal device 10 is provided in the blood flow passageway provided by the second tube 2*b*. A filter 12 is provided across the blood flow passageway 14 formed in a housing 11 with the function of stopping potential blood clots brought forward in the second tube 2*b* by the blood flow, indicated by arrows in the figure. In this preferred embodiment, the filter 12 comprises a plurality of preferably equally spaced strips 12*a* of some suitable material, such as biocompatible metal or plastic. These strips 12*a* are preferably arranged mutual parallel.

The distance between two adjacent strips is small enough to stop any blood clots. Thus, the distance is preferably less than 2 millimeters, and even more preferably less than 1.0 millimeters, but if the goal is to protect the brain from larger clots only the distance could be larger. Although the blood flow passageway 14 in the preferred embodiment has an essentially square cross-sectional shape, it will be realized that it can take any suitable shape, such as rectangular or circular.

By providing a plurality of strips 12*a* as a filter across the blood flow passageway 14, a laminar blood flow is achieved downstream of the filter, which is advantageous in a blood clot preventing perspective. The blood flow configuration can be further enhanced by giving the plurality of strips 12*a* a desired cross-sectional shape, although the rectangular shape shown in FIG. 4 will be adequate for most purposes.

A first piston 16 is provided movable in a direction essentially perpendicular to the direction of the blood flow passageway 14, i.e., essentially perpendicular to the direction of the blood flow. This first piston 16 is driven by some suitable actuator means, such as pressurized air, a solenoid arrangement, an electrical servo motor or the like. A motor could be used to build up a stored power that could be released very fast, one example being a spring. In the preferred embodiment, pressurized air acts as the actuator means, since by latching the piston by means of a suitable latching means for the piston, building up the air pressure, and subsequently releasing the piston, very high speed of the piston is achieved, with enables short cleaning times of the filter.

The outer end portion of the first piston 16, i.e., the end portion facing the blood flow passageway 14, is essentially flush with the wall of the blood flow passageway in a non-active state of the blood clot removal device 10. Also, the outer end portion is provided with a concave portion or recess 16*a* (exaggerated in the figures) in order to act as a blood clot capturing means, as will be explained below.

The strike range of the first piston 16 is such that it extends all way across the blood flow passageway 14, as will be explained below with reference to FIGS. 5-8. A number of channels 16*b* corresponding to the number of strips 12*a* is provided in the first piston 16 to accommodate the strips when the first piston is in an extended position.

The first piston 16 is also provided with a plurality of through holes 17 in the direction of the blood flow passageway. These through holes will allow blood to flow through the blood flow passageway also during a cleaning operation, as will be explained below with reference to FIG. 9.

A second piston 18 is provided across the blood flow passageway 14 from the first piston 16. Also this second piston 18 is movable in a direction essentially perpendicular to the direction of the blood flow passageway 14 and is biased in the direction thereof by means of a spring 18*a*, for example. Likewise, the outer end portion of the second piston is provided with a recess 18*b* similar to the recess 16*a* of the first piston 16.

The first and second pistons 16, 18, are sealed to the housing 11 by means of a respective sealing 20, such as an O sealing.

Figure 5:
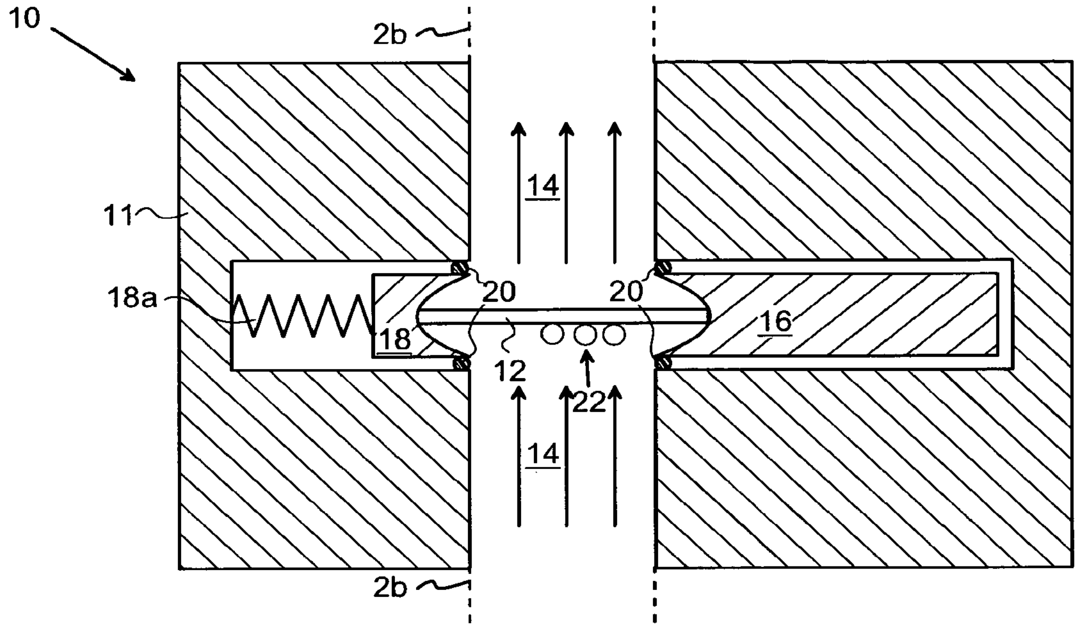
FIG. 5 is a sectional view similar to that of FIG. 2 showing blood clots before a clot removal operation.

A preferred embodiment of the method according to the invention will now be described with reference to FIGS. 5-8, showing different operational steps of the above-described device. FIG. 5 is a view similar to that of FIG. 2. However, this figures shows the blood clot removal device 10 during operation, wherein blood clots, generally designated 22, have assembled on the filter 12.

Figure 6:
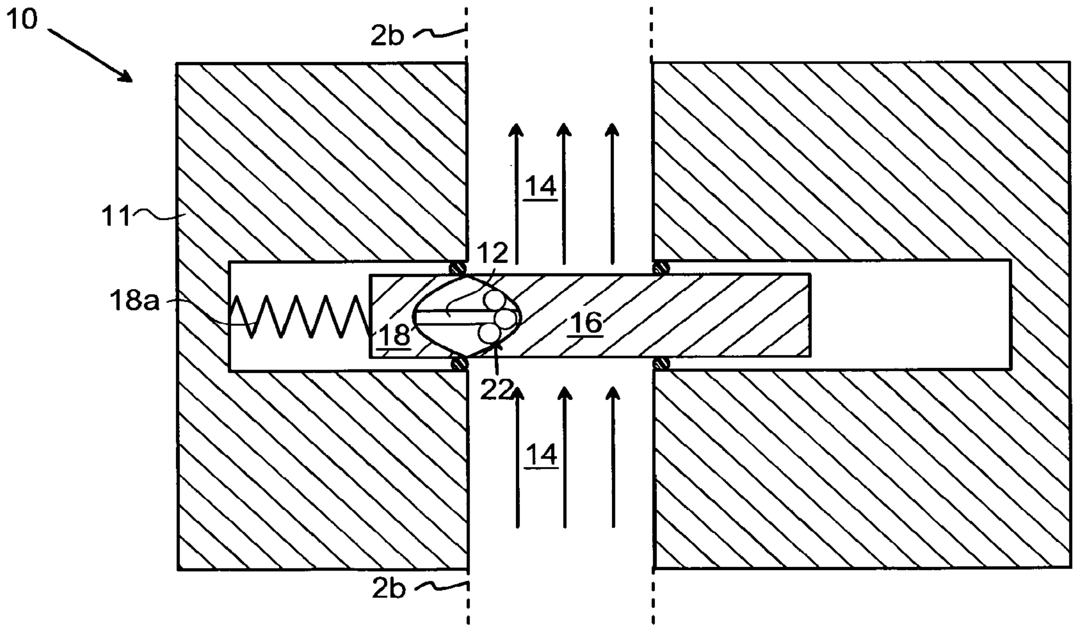
FIG. 6 is a sectional view similar to that of FIG. 2 during a first step of a clot removal operation.

In FIG. 6, the first piston 16 has moved linearly from the retracted starting position shown FIG. 5 to an extended position, wherein the outer end portion thereof is in contact with the second piston 18. Due to the recess 16*a* in the outer end of the first piston 16, the blood clots 22 have been assembled in the recess 16*a*, whereby they have been brought with the first piston 16 during the movement thereof. In the step shown in FIG. 6, the blood clots are confined in the recess 16*a* between the first and second pistons 16, 18.

Figure 7:
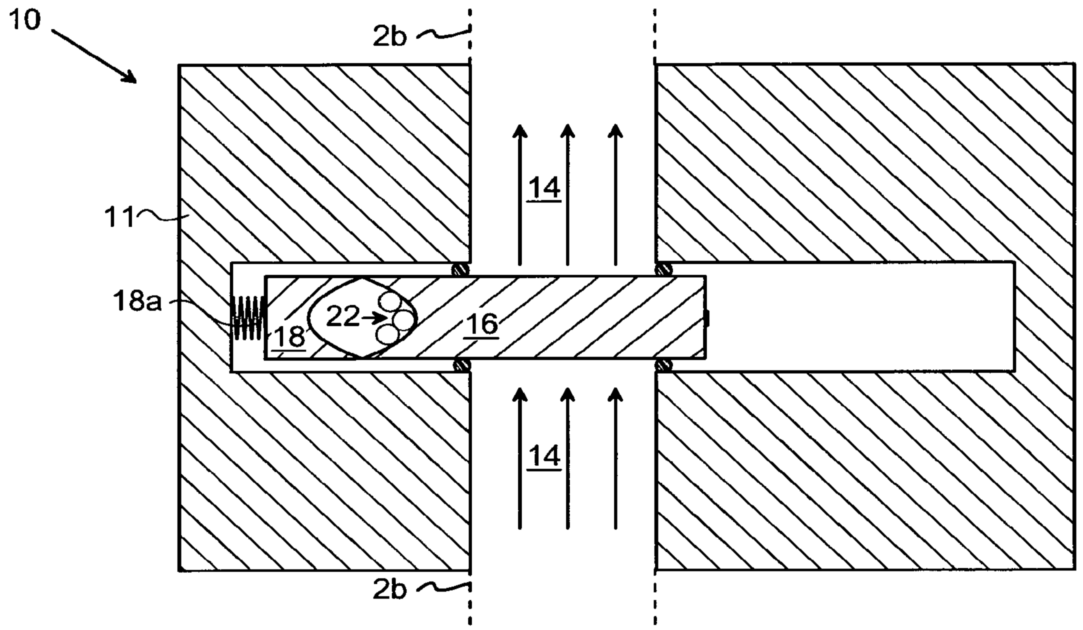
FIG. 7 is a sectional view similar to that of FIG. 2 during a second step of a clot removal operation.

By moving the first piston 16 an additional distance from the position shown in FIG. 6, the second piston 18 is pushed against the force of the spring 18*a* to a fully retracted position, see FIG. 7. The plurality of strips 12*a* is in this position fully received in a respective channel 16*b* in the first piston. It is seen that the outer ends of the first and second pistons define an unobstructed cavity in which the blood clots are confined. It is thereby possible to remove these by some suitable means. One such means could be a third piston 24, which is movable in a direction perpendicular to both the direction of the blood flow passageway 14 and the direction of movement of the first and second pistons 16, 18. This third piston, the movement of which could be controlled by means of pressurized air, a solenoid, an electric motor etc., scrapes off the blood clots collected by the first piston 16 and moves them to a place outside of the blood clot removal device 10 and the blood flow passageway 14.

Figure 8:
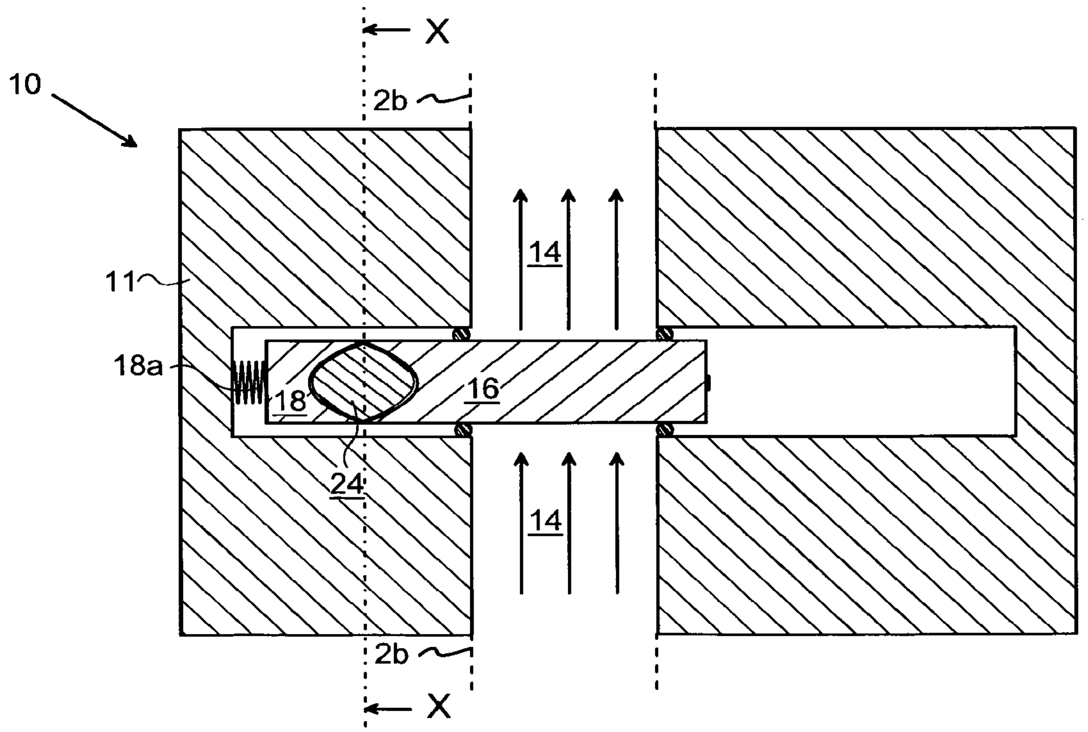
FIG. 8 is a sectional view similar to that of FIG. 2 during a third step of a clot removal operation.
Figure 9:
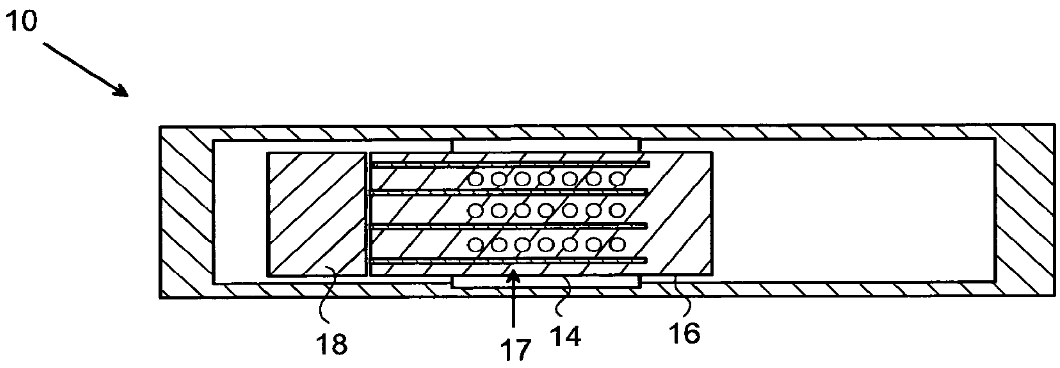
FIG. 9 is a cross sectional view similar to that of FIG. 3 but during a cleaning operation.

FIG. 9 shows a side view of the first piston 16 in a fully extended position, i.e., corresponding to the view of FIG. 8. It is here seen that in this position the through holes 17 will be aligned with the blood flow passageway 14, thereby allowing blood to flow therethrough also during cleaning of the filter 12.

Figure 10:
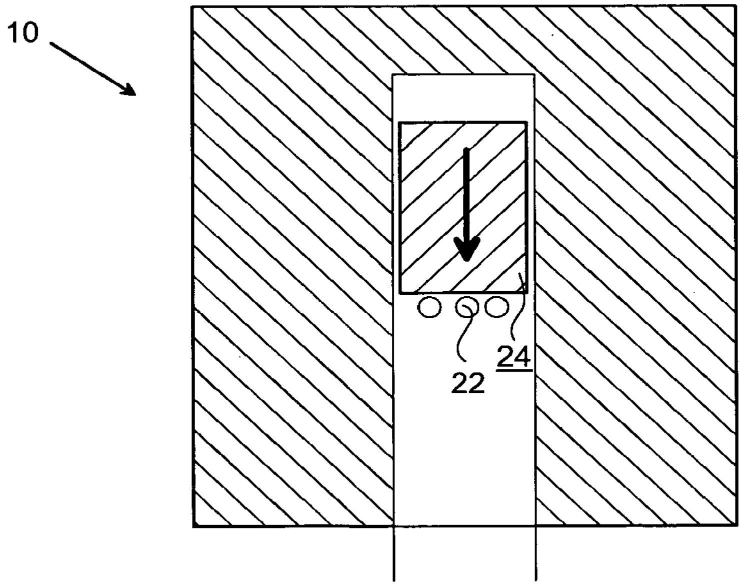
FIG. 10 is a sectional view of the clot removal device of FIG. 8 taken along the line X-X showing a clot ejection piston before ejection of clots.
Figure 11:
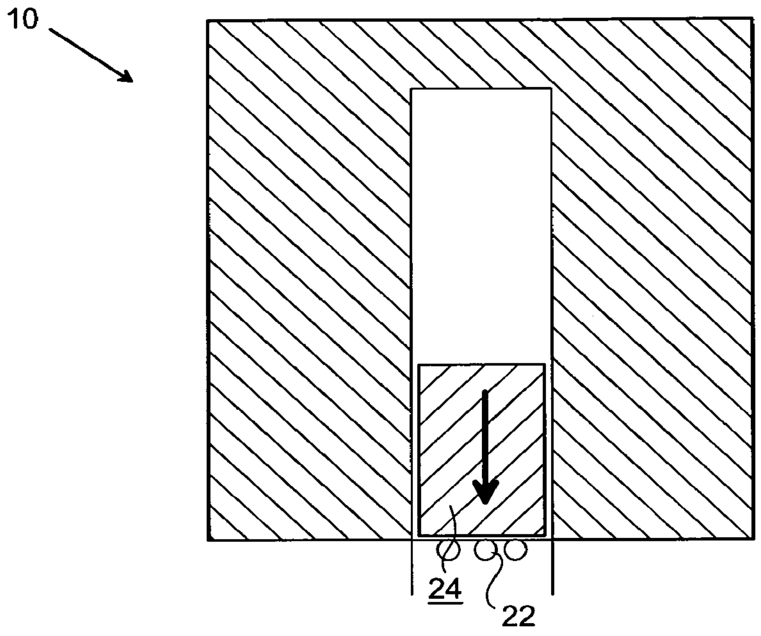
FIG. 11 is a view similar to that of FIG. 9 but after ejection of clots.

FIG. 10 shows a cross-sectional view taken along line X-X of FIG. 8. It is here seen that the third piston 24 collects the blood clots 22 during a downward movement, indicated by an arrow in the figure. The clots are ejected from the blood clot removal device 10 when the third piston 24 has reached its lower end position, shown in FIG. 11.

Again with reference to FIG. 7, it will be realized that pressurized air can be used for ejecting the collected blood clots from the cavity formed by the first piston 16 and the second piston 18.

A clot removal system, generally designated 28 and comprising a clot removal device as described above will now be described with reference to FIGS. 12-25.

Figure 12:
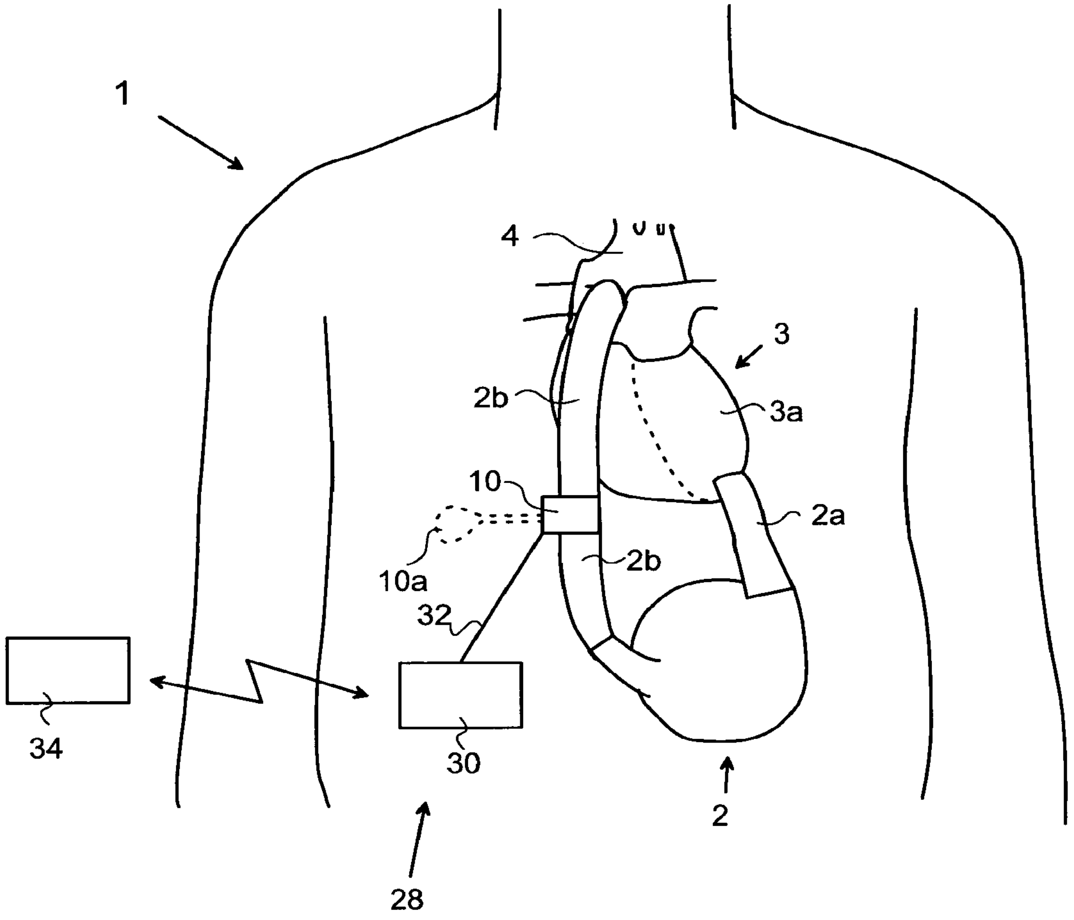
FIG. 12 is an overall view of a clot removal system according to the invention.

The system of FIG. 12 comprises a blood clot removal device 10 placed in the abdomen of the patient. An internal energy source in the form of an implanted energy transforming device 30 is adapted to supply energy consuming components of the blood clot removal device 10 with energy via a power supply line 32. An external energy transmission device 34 includes a wireless remote control transmitting a wireless signal, which is received by a signal receiver incorporated in the implanted energy transforming device 30. The implanted energy transforming device 30 transforms energy from the signal into electric energy which is supplied via the power supply line 32.

Figure 13:
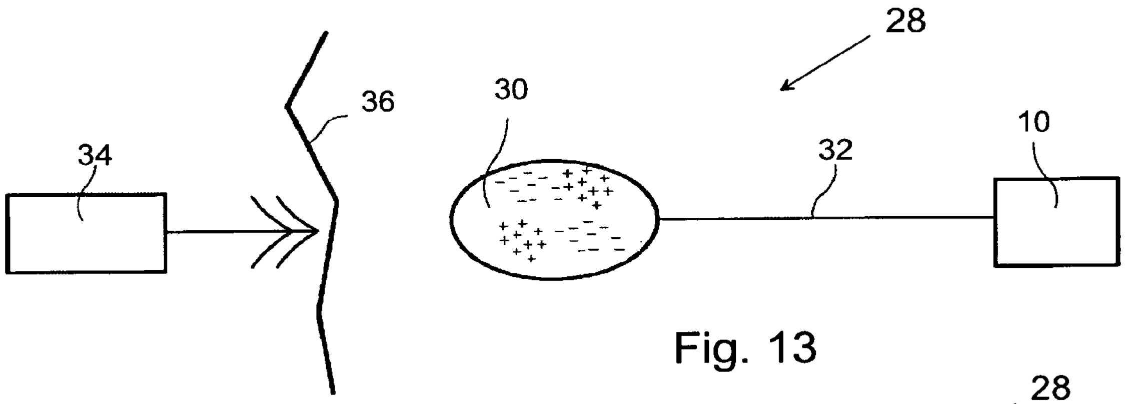
FIG. 13 is a schematic diagram of the system of FIG. 12.

The system of FIG. 12 is shown in a more generalized block diagram form in FIG. 13, wherein the patient's skin 36, generally shown by a vertical line, separates the interior of the patient to the right of the line from the exterior to the left of the line.

Figure 14:
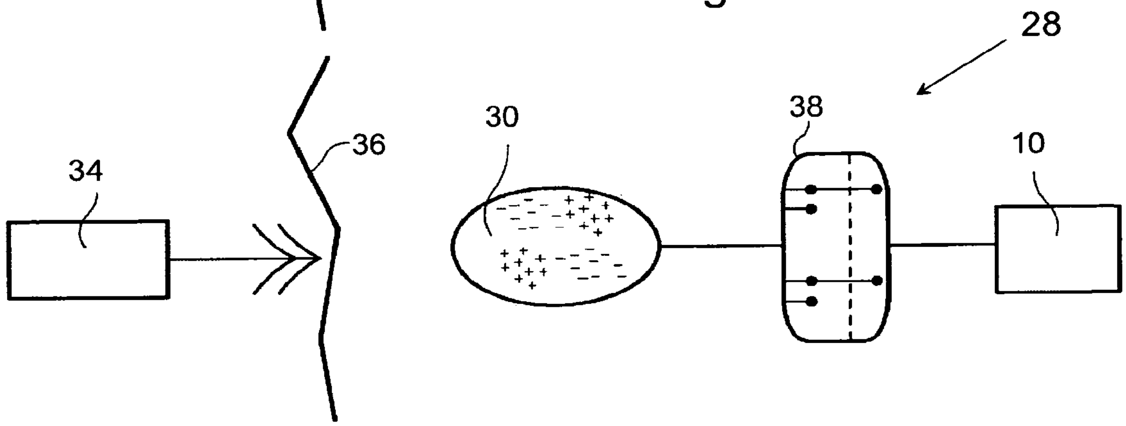
FIGS. 14-29 show various embodiments based on the system of FIG. 13.

FIG. 14 shows an embodiment of the invention identical to that of FIG. 13, except that a reversing device in the form of an electric switch 38 operable by polarized energy also is implanted in the patient for reversing the blood clot removal device 10. The wireless remote control of the external energy transmission device 34 transmits a wireless signal that carries polarized energy and the implanted energy transforming device 30 transforms the wireless polarized energy into a polarized current for operating the electric switch 38. When the polarity of the current is shifted by the implanted energy transforming device 30 the electric switch 38 reverses the function performed by the blood clot removal device 10.

Figure 15:
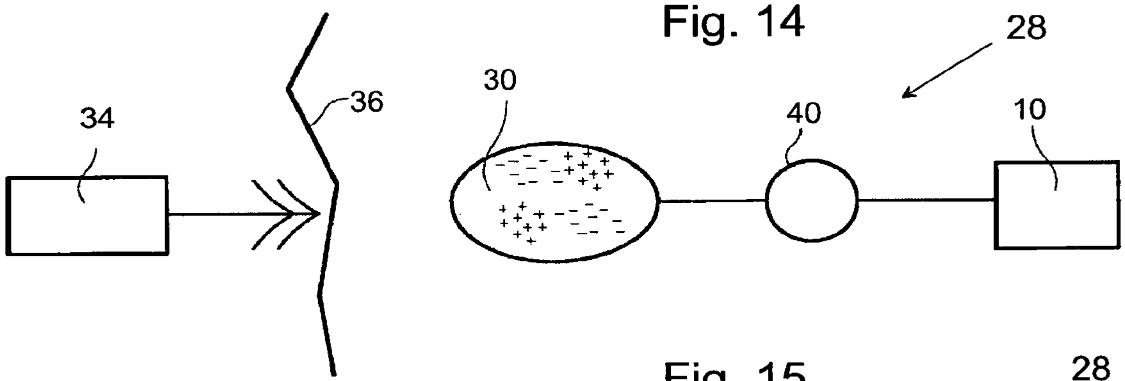

FIG. 15 shows an embodiment of the invention identical to that of FIG. 13, except that an operation device 40 implanted in the patient for regulating the blood clot removal device 10 is provided between the implanted energy transforming device 30 and the blood clot removal device 10. This operation device can be in the form of a motor 40, such as an electric servo motor. The motor 40 is powered with energy from the implanted energy transforming device 30, as the remote control of the external energy transmission device 34 transmits a wireless signal to the receiver of the implanted energy transforming device 30.

Figure 16:
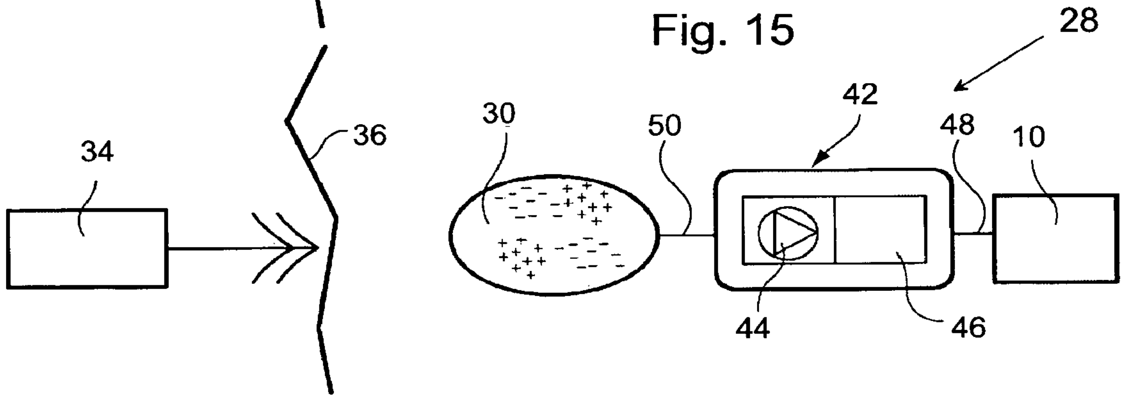

FIG. 16 shows an embodiment of the invention identical to that of FIG. 13, except that it also comprises an operation device is in the form of an assembly 42 including a motor/pump unit 78 and a fluid reservoir 46 is implanted in the patient. In this case the blood clot removal device 10 is hydraulically operated, i.e. hydraulic fluid is pumped by the motor/pump unit 44 from the fluid reservoir 46 through a conduit 48 to the blood clot removal device 10 to operate the clot removal device, and hydraulic fluid is pumped by the motor/pump unit 44 back from the blood clot removal device to the fluid reservoir 46 to return the clot removal device to a starting position. The implanted energy transforming device 30 transforms wireless energy into a current, for example a polarized current, for powering the motor/pump unit 44 via an electric power supply line 50.

Instead of a hydraulically operated blood clot removal device 10, it is also envisaged that the operation device comprises a pneumatic operation device. In this case, pressurized air can be used for regulation and the fluid reservoir is replaced by an air chamber and the fluid is replaced by air.

Figure 17:
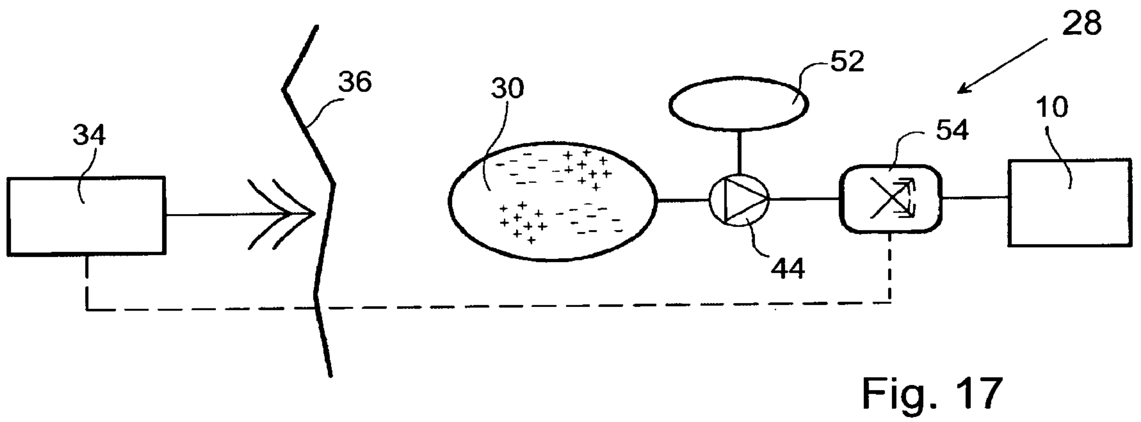

FIG. 17 shows an embodiment of the invention comprising the external energy transmission device 34 with its wireless remote control, the blood clot removal device 10, in this case hydraulically operated, and the implanted energy transforming device 30, and further comprising a hydraulic fluid reservoir 52, a motor/pump unit 44 and an reversing device in the form of a hydraulic valve shifting device 54, all implanted in the patient. The motor of the motor/pump unit 44 is an electric motor. In response to a control signal from the wireless remote control of the external energy transmission device 34, the implanted energy transforming device 30 powers the motor/pump unit 44 with energy from the energy carried by the control signal, whereby the motor/pump unit 44 distributes hydraulic fluid between the hydraulic fluid reservoir 52 and the blood clot removal device 10. The remote control of the external energy transmission device 34 controls the hydraulic valve shifting device 54 to shift the hydraulic fluid flow direction between one direction in which the fluid is pumped by the motor/pump unit 44 from the hydraulic fluid reservoir 52 to the blood clot removal device 10 to operate the clot removal device, and another opposite direction in which the fluid is pumped by the motor/pump unit 44 back from the blood clot removal device 10 to the hydraulic fluid reservoir 52 to return the clot removal device to a starting position.

Figure 18:
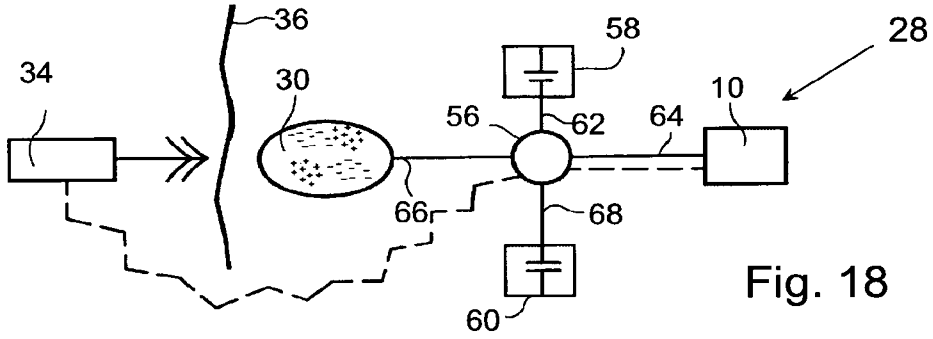

FIG. 18 shows an embodiment of the invention identical to that of FIG. 13, except that an internal control unit 56 controlled by the wireless remote control of the external energy transmission device 34, an accumulator 58 and a capacitor 60 also are implanted in the patient. The internal control unit 56 arranges storage of electric energy received from the implanted energy transforming device 30 in the accumulator 58, which supplies energy to the blood clot removal device 10. In response to a control signal from the wireless remote control of the external energy transmission device 34, the internal control unit 56 either releases electric energy from the accumulator 58 and transforms the released energy via power lines 62 and 64, or directly transforms electric energy from the implanted energy transforming device 30 via a power line 66, the capacitor 60, which stabilizes the electric current, a power line 68 and the power line 64, for the operation of the blood clot removal device 10.

The internal control unit is preferably programmable from outside the patient's body. In a preferred embodiment, the internal control unit is programmed to regulate the blood clot removal device 10 to remove any blood clots from the vascular system and place the blood clots outside the vascular system repeatedly according to a pre-programmed time-schedule.

In accordance with an alternative, the capacitor 60 in the embodiment of FIG. 18 may be omitted. In accordance with another alternative, the accumulator 58 in this embodiment may be omitted.

Figure 19:
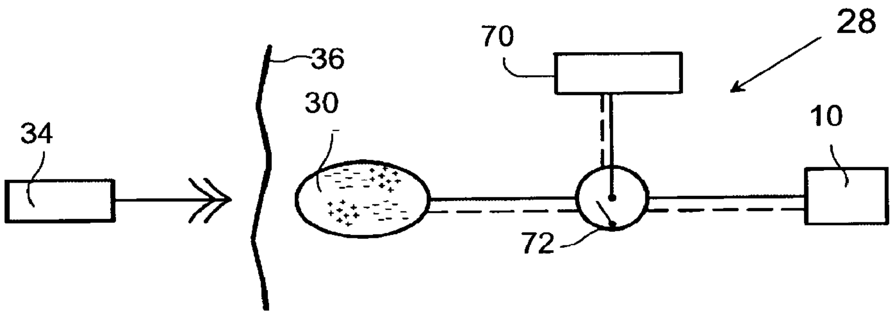

FIG. 19 shows an embodiment of the invention identical to that of FIG. 13, except that a battery 70 for supplying energy for the operation of the blood clot removal device 10 and an electric switch 72 for switching the operation of the blood clot removal device 10 also are implanted in the patient. The electric switch 72 is operated by the energy supplied by the implanted energy transforming device 30 to switch from an off mode, in which the battery 70 is not in use, to an on mode, in which the battery 70 supplies energy for the operation of the blood clot removal device 10.

Figure 20:
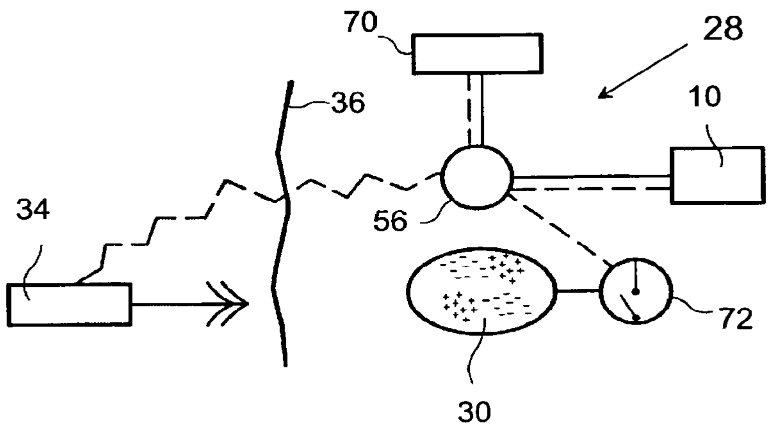

FIG. 20 shows an embodiment of the invention identical to that of FIG. 19, except that an internal control unit 56 controllable by the wireless remote control of the external energy transmission device 34 also is implanted in the patient. In this case, the electric switch 72 is operated by the energy supplied by the implanted energy transforming device 30 to switch from an off mode, in which the wireless remote control is prevented from controlling the internal control unit 56 and the battery is not in use, to a standby mode, in which the remote control is permitted to control the internal control unit 56 to release electric energy from the battery 70 for the operation of the blood clot removal device 10.

Figure 21:
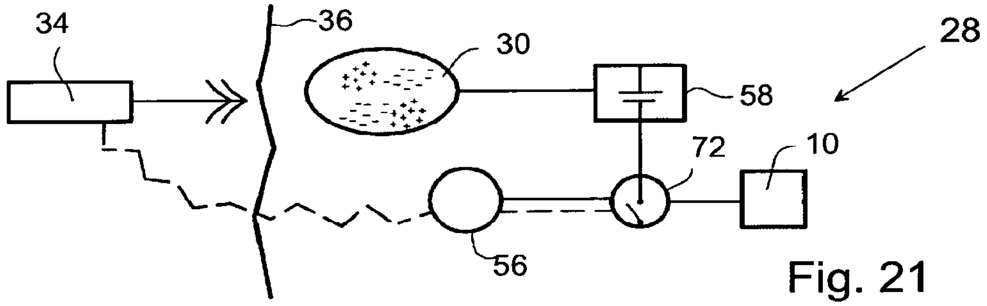

FIG. 21 shows an embodiment of the invention identical to that of FIG. 20, except that an accumulator 58 is substituted for the battery 70 and the implanted components are interconnected differently. In this case, the accumulator 58 stores energy from the implanted energy transforming device 30. In response to a control signal from the wireless remote control of the external energy transmission device 34, the internal control unit 56 controls the electric switch 72 to switch from an off mode, in which the accumulator 58 is not in use, to an on mode, in which the accumulator 58 supplies energy for the operation of the blood clot removal device 10.

Figure 22:
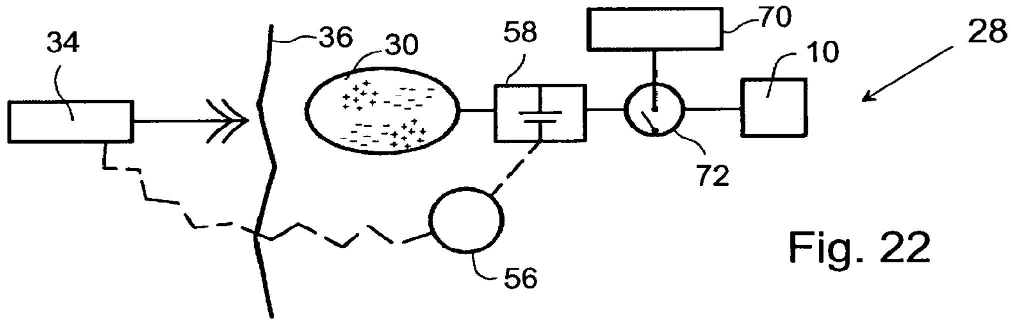

FIG. 22 shows an embodiment of the invention identical to that of FIG. 21, except that a battery 70 also is implanted in the patient and the implanted components are interconnected differently. In response to a control signal from the wireless remote control of the external energy transmission device 34, the internal control unit 56 controls the accumulator 58 to deliver energy for operating the electric switch 72 to switch from an off mode, in which the battery 70 is not in use, to an on mode, in which the battery 70 supplies electric energy for the operation of the blood clot removal device 10.

Alternatively, the electric switch 72 may be operated by energy supplied by the accumulator 58 to switch from an off mode, in which the wireless remote control is prevented from controlling the battery 70 to supply electric energy and is not in use, to a standby mode, in which the wireless remote control is permitted to control the battery 70 to supply electric energy for the operation of the blood clot removal device 10.

Figure 23:
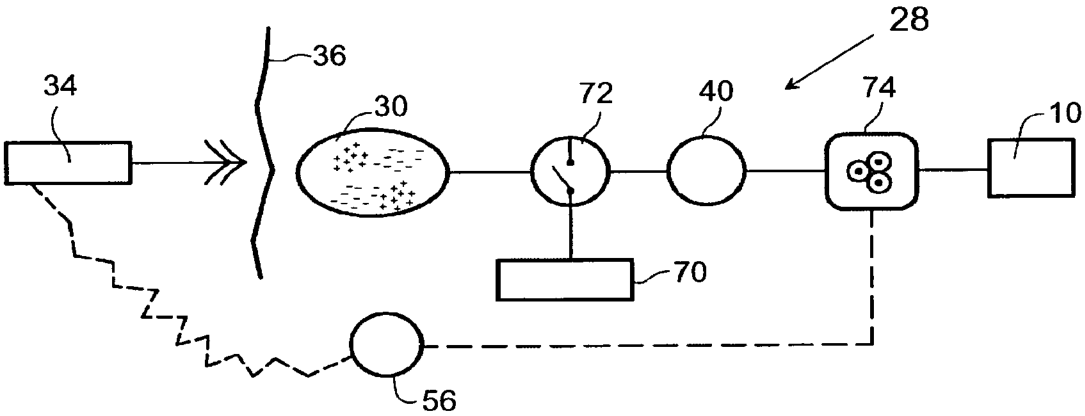

FIG. 23 shows an embodiment of the invention identical to that of FIG. 19, except that a motor 40, a mechanical reversing device in the form of a gear box 74, and an internal control unit 56 for controlling the gear box 74 also are implanted in the patient. The internal control unit 56 controls the gear box 74 to reverse the function performed by the blood clot removal device 10 (mechanically operated).

Figure 24:
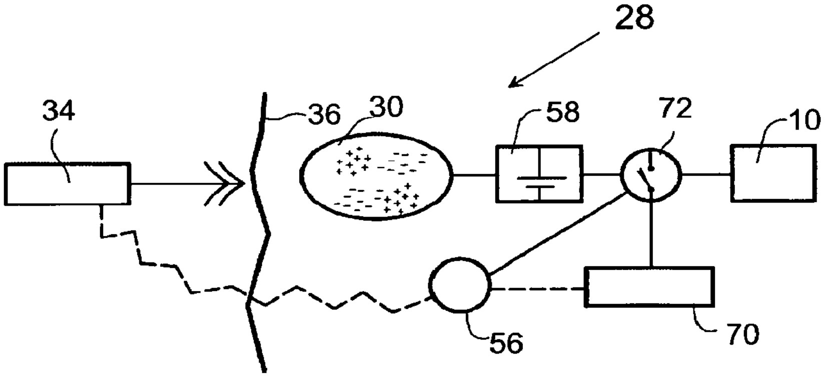

FIG. 24 shows an embodiment of the invention identical to that of FIG. 22 except that the implanted components are interconnected differently. Thus, in this case the internal control unit 56 is powered by the battery 70 when the accumulator 58, suitably a capacitor, activates the electric switch 72 to switch to an on mode. When the electric switch 72 is in its on mode the internal control unit 56 is permitted to control the battery 70 to supply, or not supply, energy for the operation of the blood clot removal device 10.

Figure 25:
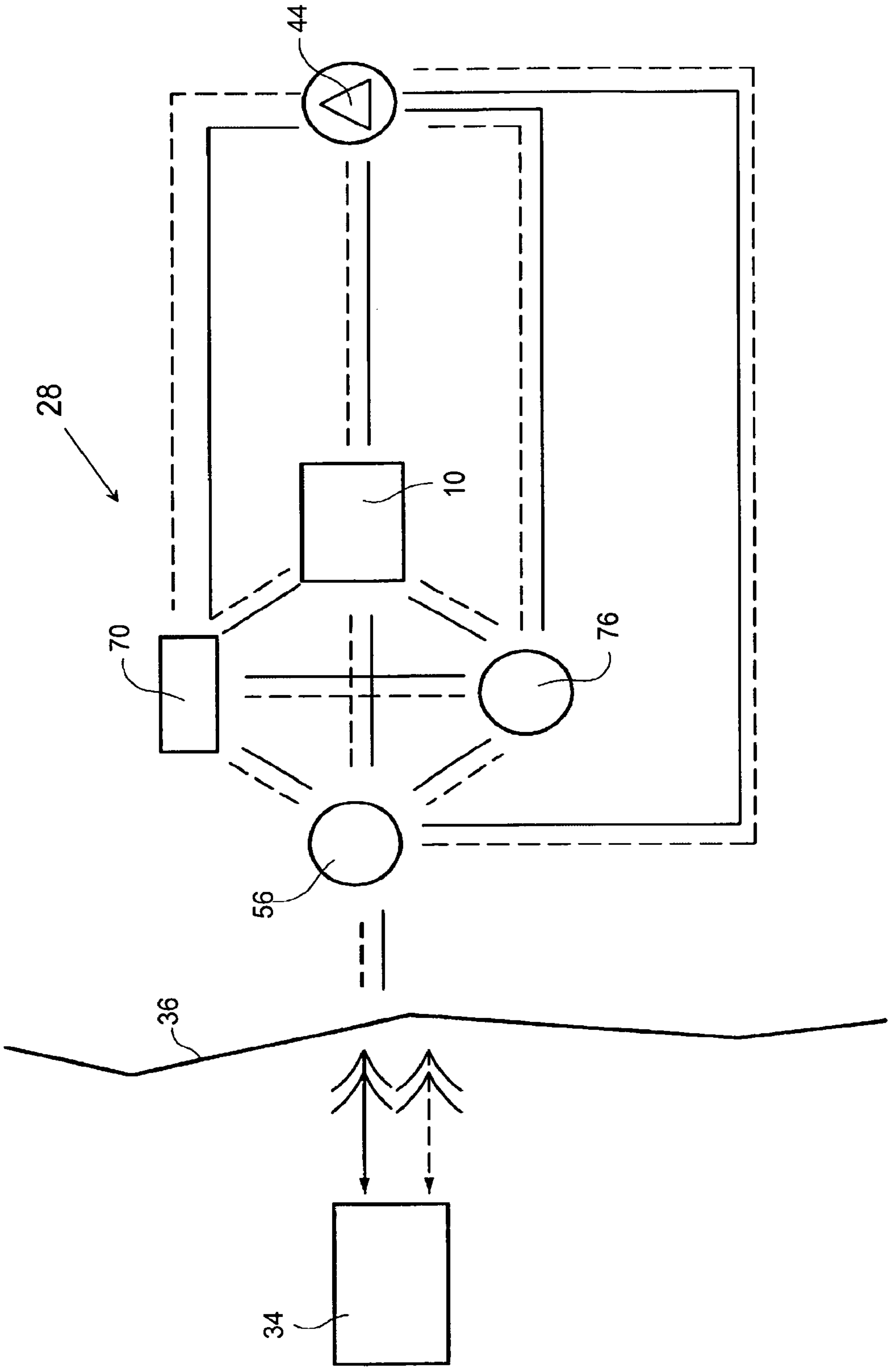

FIG. 25 schematically shows conceivable combinations of implanted components of the apparatus for achieving various communication options. Basically, there are the blood clot removal device 10, the internal control unit 56, motor/pump unit 44, and the external energy transmission device 34 including the external wireless remote control. As already described above the wireless remote control transmits a control signal which is received by the internal control unit 56, which in turn controls the various implanted components of the apparatus.

A feedback device, preferably in the form of a sensor 76, may be implanted in the patient for sensing a physical parameter of the patient, such as the pressure in a blood vessel. The internal control unit 56, or alternatively the external wireless remote control of the external energy transmission device 34, may control the blood clot removal device 10 in response to signals from the sensor 76. A transceiver may be combined with the sensor 76 for sending information on the sensed physical parameter to the external wireless remote control. The wireless remote control may comprise a signal transmitter or transceiver and the internal control unit 56 may comprise a signal receiver or transceiver. Alternatively, the wireless remote control may comprise a signal receiver or transceiver and the internal control unit 56 may comprise a signal transmitter or transceiver. The above transceivers, transmitters and receivers may be used for sending information or data related to the blood clot removal device 10 from inside the patient's body to the outside thereof.

Alternatively, the sensor 76 may be arranged to sense a functional parameter of the blood clot removal device 10.

Where the motor/pump unit 44 and battery 70 for powering the motor/pump unit 44 are implanted, the battery 70 may be equipped with a transceiver for sending information on the condition of the battery 70.

Figure 26:
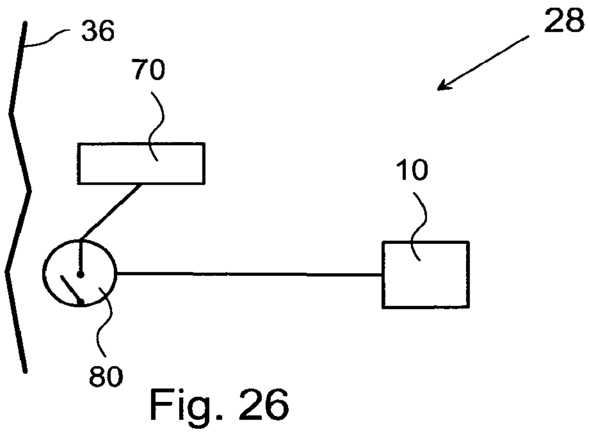

FIG. 26 shows an alternative embodiment wherein the blood clot removal device 10 is regulated from outside the patient's body. The clot removal system 28 comprises a blood clot removal device 10 connected to a battery 70 via a subcutaneous switch 80. Thus, the regulation of the blood clot removal device 10 is performed non-invasively by manually pressing the subcutaneous switch, whereby the operation of the blood clot removal device 10 is switched on and off. It will be appreciated that the shown embodiment is a simplification and that additional components, such as an internal control unit, can be added to the clot removal system.

Figure 27:
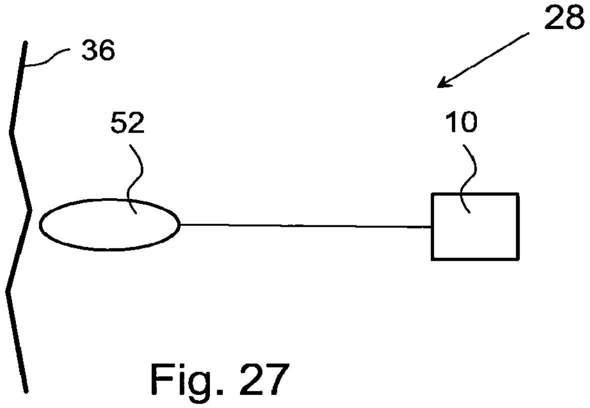

FIG. 27 shows an alternative embodiment, wherein the clot removal system 28 comprises a blood clot removal device 10 in fluid connection with a hydraulic fluid reservoir 52. Non-invasive regulation is performed by manually pressing the hydraulic reservoir connected to the blood clot removal device 10.

A further embodiment of a system according to the invention comprises a feedback device for sending information from inside the patient's body to the outside thereof to give feedback information related to at least one functional parameter of the clot removal device or system or a physical parameter of the patient, thereby optimizing the performance of the system.

One preferred functional parameter of the device is correlated to the transfer of energy for charging the internal energy source.

Figure 28:
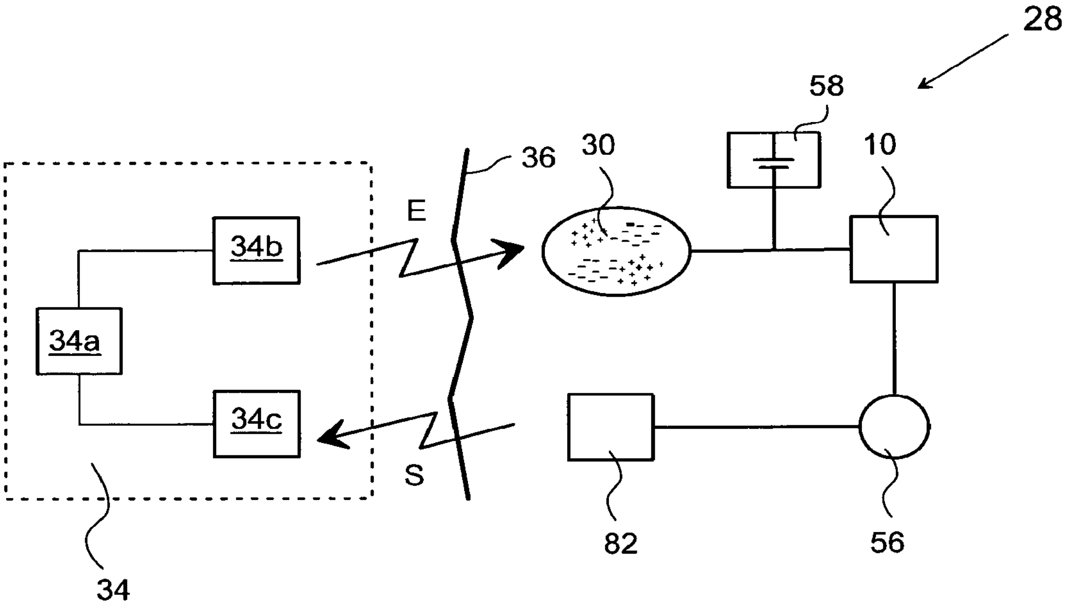

In FIG. 28, an arrangement is schematically illustrated for supplying an accurate amount of energy to a clot removal system 28 implanted in a patient, whose skin 36 is indicated by a vertical line. A blood clot removal device 10 is connected to an implanted energy transforming device 30, likewise located inside the patient, preferably just beneath the patient's skin 36. Generally speaking, the implanted energy transforming device 30 may be placed in the abdomen, thorax, muscle fascia (e.g. in the abdominal wall), subcutaneously, or at any other suitable location. The the implanted energy transforming device 30 is adapted to receive wireless energy E transmitted from an external energy source 34*a* provided in the external energy transmission device 34 located outside the patient's skin 36 in the vicinity of the implanted energy transforming device 30.

As is well known in the art, the wireless energy E may generally be transferred by means of any suitable Transcutaneous Energy Transfer (TET) device, such as a device including a primary coil arranged in the external energy source 34*a* and an adjacent secondary coil arranged in the implanted energy transforming device 30.

When an electric current is fed through the primary coil, energy in the form of a voltage is induced in the secondary coil which can be used to operate a clot removal device, e.g. after storing the incoming energy in an energy storing device or accumulator, such as a battery or a capacitor. However, the present invention is generally not limited to any particular energy transfer technique, TET devices or energy storing devices, and any kind of wireless energy may be used.

The amount of transferred energy can be regulated by means of an external control unit 34*b* controlling the external energy source 34*a* based on the determined energy balance, as described above. In order to transfer the correct amount of energy, the energy balance and the required amount of energy can be determined by means of an internal control unit 56 connected to the blood clot removal device 10. The internal control unit 56 may thus be arranged to receive various measurements obtained by suitable sensors or the like, not shown, measuring certain characteristics of the blood clot removal device 10, somehow reflecting the required amount of energy needed for proper operation of the blood clot removal device 10. Moreover, the current condition of the patient may also be detected by means of suitable measuring devices or sensors, in order to provide parameters reflecting the patient's condition. Hence, such characteristics and/or parameters may be related to the current state of the blood clot removal device 10, such as power consumption, operational mode and temperature, as well as the patient's condition reflected by, e.g., body temperature, blood pressure, heartbeats and breathing.

Furthermore, an energy storing device or accumulator 58 may optionally be connected to the implanted energy transforming device 30 for accumulating received energy for later use by the blood clot removal device 10. Alternatively or additionally, characteristics of such an accumulator, also reflecting the required amount of energy, may be measured as well. The accumulator may be replaced by a battery, and the measured characteristics may be related to the current state of the battery, such as voltage, temperature, etc. In order to provide sufficient voltage and current to the blood clot removal device 10, and also to avoid excessive heating, it is clearly understood that the battery should be charged optimally by receiving a correct amount of energy from the implanted energy transforming device 30, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 56. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 56 is adapted to determine the energy balance and/or the currently required amount of energy, (either energy per time unit or accumulated energy) based on measurements made by the above-mentioned sensors or measuring devices on the blood clot removal device 10, or the patient, or an energy storing device if used, or any combination thereof. The internal control unit 56 is further connected to an internal signal transmitter 82, arranged to transmit a control signal reflecting the determined required amount of energy, to an external signal receiver 34*c* connected to the external control unit 34*b*. The amount of energy transmitted from the external energy source 34*a* may then be regulated in response to the received control signal.

Alternatively, sensor measurements can be transmitted directly to the external control unit 34*b* wherein the energy balance and/or the currently required amount of energy can be determined by the external control unit 34*b*, thus integrating the above-described function of the internal control unit 56 in the external control unit 34*b*. In that case, the internal control unit 56 can be omitted and the sensor measurements are supplied directly to the internal signal transmitter 82 which sends the measurements over to the external signal receiver 34*c* and the external control unit 34*b*. The energy balance and the currently required amount of energy can then be determined by the external control unit 34*b* based on those sensor measurements.

Hence, the present solution employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by the clot removal device. The clot removal device may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the clot removal device.

The internal signal transmitter 82 and the external signal receiver 34*c* may be implemented as separate units using suitable signal transfer means, such as radio, IR (Infrared) or ultrasonic signals. Alternatively, the internal signal transmitter 82 and the external signal receiver 34*c* may be integrated in the implanted energy transforming device 30 and the external energy source 34*a*, respectively, so as to convey control signals in a reverse direction relative to the energy transfer, basically using the same transmission technique. The control signals may be modulated with respect to frequency, phase or amplitude.

To conclude, the energy supply arrangement illustrated in FIG. 28 may operate basically in the following manner. The energy balance is first determined by the internal control unit 56. A control signal reflecting the required amount of energy is also created by the internal control unit 56, and the control signal is transmitted from the internal signal transmitter 82 to the external signal receiver 34*c*. Alternatively, the energy balance can be determined by the external control unit 34*b* instead depending on the implementation, as mentioned above. In that case, the control signal may carry measurement results from various sensors. The amount of energy emitted from the external energy source 34*a* can then be regulated by the external control unit 34*b*, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 34*a*, such as voltage, current, amplitude, wave frequency and pulse characteristics.

A method is thus provided for controlling transmission of wireless energy supplied to an electrically operable clot removal device implanted in a patient. The wireless energy E is transmitted from an external energy source located outside the patient and is received by an internal energy receiver located inside the patient, the internal energy receiver being connected to the clot removal device for directly or indirectly supplying received energy thereto. An energy balance is determined between the energy received by the internal energy receiver and the energy used for the clot removal device. The transmission of wireless energy E from the external energy source is then controlled based on the determined energy balance.

A system is also provided for controlling transmission of wireless energy supplied to an electrically operable clot removal device implanted in a patient. The system is adapted to transmit the wireless energy E from an external energy source located outside the patient which is received by an implanted energy transforming device located inside the patient, the implanted energy transforming device being connected to the clot removal device for directly or indirectly supplying received energy thereto. The system is further adapted to determine an energy balance between the energy received by the implanted energy transforming device and the energy used for the clot removal device, and control the transmission of wireless energy E from the external energy source, based on the determined energy balance.

The functional parameter of the device is correlated to the transfer of energy for charging the internal energy source.

In yet an alternative embodiment, the external source of energy is controlled from outside the patient's body to release electromagnetic wireless energy, and released electromagnetic wireless energy is used for operating the blood clot removal device.

In another embodiment, the external source of energy is controlling from outside the patient's body to release non-magnetic wireless energy, and released non-magnetic wireless energy is used for operating the blood clot removal device.

Those skilled in the art will realize that the above various embodiments according to FIGS. 13-29 could be combined in many different ways. For example, the electric switch 38 operated polarized energy could be incorporated in any of the embodiments of FIGS. 15, 18-24, the hydraulic valve shifting device 54 could be incorporated in the embodiment of FIG. 16, and the gear box 74 could be incorporated in the embodiment of FIG. 15.

Figure 29:
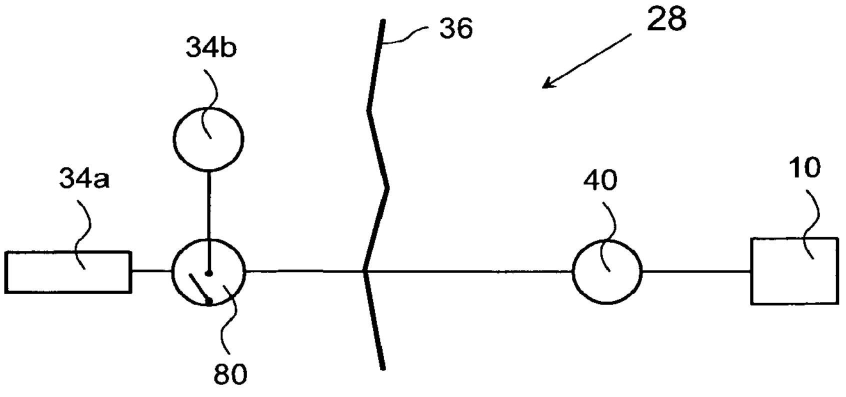

Wireless transfer of energy for operating the clot removal device has been described to enable non-invasive operation. It will be appreciated that the clot removal device can be operated with wire bound energy as well. On such example is shown in FIG. 29, wherein an external switch 84 is interconnected between the external energy source 34*a* and an operation device, such as an electric motor regulating the blood clot removal device 10, by means of power lines 86 and 88. An external control unit 34*b* controls the operation of the external switch to effect proper operation of the blood clot removal device 10.

Methods relating to the above described clot removal device and system will now be described in detail.

The clot removal device can be placed surgically in the patient via a laparoscopic abdominal approach. First, a tube is inserted into the abdomen of the patient's body and this tube is used to fill the patient's abdomen with gas, thereby expanding the patient's abdominal cavity. At least two laparoscopic trocars are then placed in the patient's body, where after a camera is inserted through one of the trocars into the patient's abdomen. At least one dissecting tool is inserted through a trocar and dissection is performed at two intended areas of the patient. A clot removal device is placed in any part of the vascular system in the abdomen.

Alternatively, the clot removal device can be placed in the patient's thorax. Thus, a tube is inserted into the thorax of the patient's body and this tube is used to fill the patient's thorax with gas, thereby expanding the patient's thoraxical cavity. At least two laparoscopic trocars are then placed in the patient's body, where after a camera is inserted through one of the trocars into the patient's thorax. At least one dissecting tool is inserted through a trocar and dissection is performed at two intended areas of the patient. A clot removal device is placed in any part of the vascular system in the thorax.

An operation method for surgically placing a clot removal device starts with cutting the patient's skin and dissecting a placement area where to place the clot removal device inside the vascular system in the abdomen or thorax or retroperitoneal or subcutaneously or any limb of the patient. When a suitable place has been found, the clot removal device is placed in the placement area. The clot removal device can then be used postoperatively and non-invasively without penetrating the patent's skin for removing any blood clots from the vascular system to outside thereof, while using energy from an energy source without any penetration through the patient's skin to power the blood clot removal device.

A method for surgically treating a patient needing a blood clot removal device in the vascular system in the patient's abdomen preferably comprises cutting an opening in the patient's abdominal wall and then dissecting an area of the vascular system. A clot removal device is placed inside the vascular system, and the abdominal wall is sutured. In one embodiment, blood clots are moved away from the vascular system into an encapsulated closed bag in the patient's abdomen by means of the blood clot removal device. In another embodiment, blood clots are moved to the free abdomen.

Alternatively, a method for surgically treating a patient needing a blood clot removal device in the vascular system in the thorax comprises cutting an opening in the thorax wall and then dissecting the area of the vascular system. A clot removal device is placed inside the vascular system, and the thorax wall is sutured. A step of moving blood clots away from the vascular system can comprise moving blood clots either to a place that is free in the thorax, to a place that is free in the abdomen, or to a place that is encapsulated in a closed bag in the thorax.

In one embodiment, a method of using a system for removing blood clots comprises implanting an implantable source of energy, such as an implanted energy transforming device 30 and an accumulator 58, in the patient. An external source of energy, such as an external energy transmission device 34, is provided for providing energy to the system. This external source of energy is operated to release wireless energy, thereby non-invasively charging the implantable source of energy with the wireless energy, while controlling the implantable source of energy from outside the patient's body. In connection with operation of the clot removal device, energy is releasing. The wireless energy is preferably stored in the implantable source of energy.

During operation, the system for removing blood clots postoperatively and non-invasively regulates the clot removal device. Any blood clots, which have been accumulated in the vascular system of the patient's body, are moved away from the vascular system and are then placed outside the vascular system. This can be accomplished by an energy source, preferably repeatedly according to a pre-programmed time-schedule. The movement of any blood clots away from the vascular system and placement of the blood clots outside the vascular system are preferably repeated and at least partly controlled by an internal control unit getting input from a sensor sensing any physical parameter of the patient or any functional parameter of the device.

Preferred embodiments of a clot removal device, a system comprising a clot removal device, and a method according to the invention have been described. A person skilled in the art realizes that these could be varied within the scope of the appended claims.

The blood clot removal device has been described as an artificial device insertable in an artificial blood vessel of the patient. Alternatively, the blood clot removal device is an artificial device adapted to be placed between two open ends of a blood vessel of the patient or be placed inside or attached to a blood vessel via surgery.

The blood clot removal device has been described to be placed in the patient's abdomen or thorax. It could also be adapted to be placed in the patient's retroperitoneal region or cephalic or neck region or any limb of the patient.

The filter in the blood clot removal device may be exchanged and replaced with a new fresh filter when it becomes dirty. One embodiment of such a solution is described below in FIGS. 30 and 31. There are obvious many different solutions to solve the same problems.

Figure 30A:
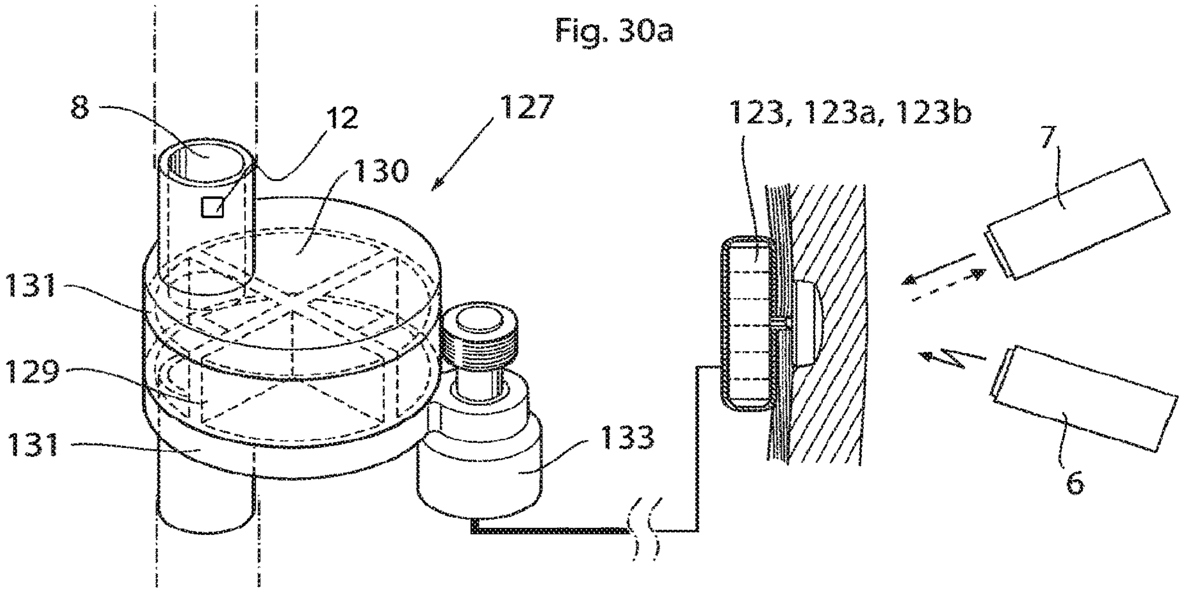
FIGS. 30*a* and 30*b* are views of a filter cassette.

In FIG. 30*a* a cassette 127 for holding filters is shown. The cassette 27 comprises a revolving cylinder 129 having segments 130 each holding a filter. The cylinder 129 is tightly sealed between two supports 131 holding the cylinder 129 in place and providing a tight sealing. Preferable are the contacting surfaces made of ceramics to seal the surfaces with fine tolerances. The blood flow passageway of an implantable blood clot removal apparatus passes through the cassette 127. The cassette is driven by a motor 133 causing the cylinder 129 to revolve at suitable times. Preferable the filter is designed to move any collected blood clots out from the blood flow passageway together with revolving filter, when the filter leaves the blood flow passageway to be replaced with a new filter. The filter may be any kind of filter preferable with a space for the collected blood clots or blood clots adherent to the filter itself. Such a space to both the sealing plates when rotating, should preferable be larger before the filter seen in the blood flow passageway. The motor is powered by a power supply 123*b*. The power supply can be a power supply like the power supplies 123 or 123*a*. In accordance with one embodiment the power supplies 123, 123*a* and 123*b* is the one and same power supply. As with the power supplies 123 and 123*a*, the power supply 123*b* can receive wireless energy in a suitable form, including but not limited to inductive energy ultrasonic energy, light energy or any other form of wireless energy set out above. The energy is supplied by an external wireless energy transmitter 6 adapted to transmit energy through the skin 5 of a patient having the cassette 127 implanted. The power supply 132*b* can also comprise a control unit as described above for controlling the revolving cassette 127. The control unit can provide feedback to the outside and receive input data from an external transceiver 7 in a manner similar to the control unit used in conjunction with control of the pump.

Figure 30B:
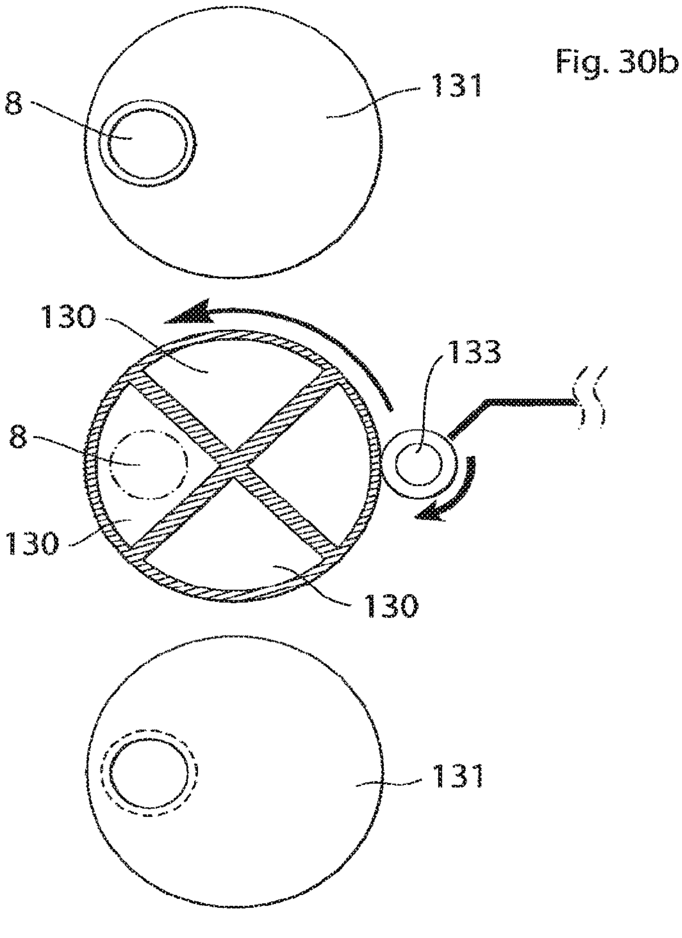

In FIG. 30*b* the cassette 127 is shown from the side with the supports 131 and the revolving cylinder spaced apart is a disassembled view.

In FIG. 31*a* an alternative embodiment of the cassette 127 is shown. The view in FIG. 30*a* is similar to the view in FIG. 31*a*. In the embodiment in FIG. 31*a* a magazine 135 having a number of cylinders 129 stored therein is provided. Hereby a cylinder 129 can by replaced by shifting the cylinders in the magazine 135. In one embodiment the cylinders are shifted by pressurized air or a motor. The filter is then first replaced in the blood flow passageway and thereafter in a position outside the blood flow passageway replaced in the cassette. Such a replacement could preferable take place by having a number of filters in the cylinder 135 on one side of the cassette marked with 135 and moving the dirty filters out from the cassette into the cylinder on the other side of the cassette.

In an alternative embodiment the cylinder 135 is instead a cleaning device adapted to clean the filter at a position outside the blood flow passageway.

In FIG. 31*b* the cassette 127 is shown from the side with the supports 131 and the revolving cylinder spaced apart is a disassembled view.

Please note that any embodiment or part of embodiment or feature or method or associated system or part of system described herein may be combined in any combination.

The invention claimed is:

1. An implantable cassette for holding filters, wherein the cassette comprises:

a revolving compartment having a plurality of segments, wherein each segment is configured to hold a filter, and wherein at least a first segment comprises a filter configured to filter blood, and attachment means for attaching the cassette to a blood flow passageway to thereby allow blood to flow through the first segment of the revolving compartment;

an operation device configured to revolve the revolving compartment, to thereby move the first segment out of the blood flow passageway.

2. The implantable cassette according to claim 1, wherein the revolution of the revolving compartment moves a second segment into the blood flow passageway.

3. The implantable cassette according to claim 1, wherein the revolving compartment comprises at least 2 segments.

4. The implantable cassette according to claim 1, wherein the revolving compartment comprises at least 3 segments.

5. The implantable cassette according to claim 1, wherein the revolving compartment comprises at least 4 segments.

6. The implantable cassette according to claim 1, further comprising a support configured to hold the compartment in place in the blood flow passageway.

7. The implantable cassette according to claim 6, further comprising a further support configured to hold the compartment in place in the blood flow passageway.

8. The implantable cassette according to claim 1, further comprising a power supply for powering the operation device.

9. The implantable cassette according to claim 8, wherein the power supply is rechargeable.

10. The implantable cassette according to claim 9, wherein the power supply is configured to be recharged by wireless energy.

11. The implantable cassette according to claim 1, further comprising a control unit for controlling the implantable cassette.

12. The implantable cassette according to claim 11, wherein the control unit comprises an implantable control device.

13. The implantable cassette according to claim 11, wherein the control unit comprises an external remote control.

14. The implantable cassette according to claim 1, wherein the operation device is configured to apply pressurized air to revolve the compartment.

15. The implantable cassette according to claim 1, wherein the operation device is an electric motor.

16. The implantable cassette according to claim 1, wherein the revolving compartment is substantially cylindrical.

17. The implantable cassette according to claim 16, wherein the substantially cylindrical revolving compartment is divided into equally large parts forming the respective segments.

18. The implantable cassette according to claim 1, further comprising a sensor configured to sense a physical parameter of the patient.

19. The implantable cassette according to claim 1, further comprising a sensor configured to sense a functional parameter of the device.

20. The implantable cassette according to claim 1, further comprising a sensor configured to sense an accumulation of blood clots in the filter.

* * * * *